(12) United States Patent
Mishra et al.

(10) Patent No.: US 11,864,586 B2
(45) Date of Patent: Jan. 9, 2024

(54) TIP DEVICE FOR ELECTRONIC VAPING DEVICE

(71) Applicant: Altria Client Services LLC, Richmond, VA (US)

(72) Inventors: Munmaya K. Mishra, Manakin Sabot, VA (US); Raymond Lau, Richmond, VA (US); Zack Blackmon, Richmond, VA (US); Kelli McKenna, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 148 days.

(21) Appl. No.: 17/329,522

(22) Filed: May 25, 2021

(65) Prior Publication Data

US 2021/0274838 A1 Sep. 9, 2021

Related U.S. Application Data

(63) Continuation of application No. 15/858,546, filed on Dec. 29, 2017, now Pat. No. 11,033,051.

(51) Int. Cl.
*A24F 47/00* (2020.01)
*A24F 13/02* (2006.01)
(Continued)

(52) U.S. Cl.
CPC ............... *A24F 13/02* (2013.01); *A24F 7/00* (2013.01); *A24F 40/30* (2020.01); *A24F 40/485* (2020.01);
(Continued)

(58) Field of Classification Search
CPC ...................................... A24F 40/30
See application file for complete search history.

(56) References Cited

U.S. PATENT DOCUMENTS

| 5,865,185 A | 2/1999 | Collins et al. |
| 6,772,757 B2 | 8/2004 | Sprinkel, Jr. |

(Continued)

FOREIGN PATENT DOCUMENTS

| CN | 103263083 A | 8/2013 |
| CN | 105120694 A | 12/2015 |

(Continued)

OTHER PUBLICATIONS

US 9,750,283 B2, 09/2017, Tucker et al. (withdrawn)

(Continued)

*Primary Examiner* — Eric Yaary
(74) *Attorney, Agent, or Firm* — Harness, Dickey & Pierce, P.L.C.

(57) ABSTRACT

A tip device for an electronic vaping device may include a first conduit structure and a second conduit structure. The first conduit structure may be configured to direct a generated vapor through a first conduit. The second conduit structure may be configured to direct an air flow from an ambient environment through a second conduit. The second conduit structure may include an additive material on a surface of the second conduit structure, the additive material including an additive, the additive material configured to release the additive into the air flow directed through the second conduit. An interposing structure of the first conduit structure and the second conduit structure may physically isolate the additive material from the first conduit, such that the additive material is configured to release the additive into the air flow directed through the second conduit independently of the generated vapor directed through the first conduit.

20 Claims, 13 Drawing Sheets

(51) Int. Cl.
*A61M 15/00* (2006.01)
*A24F 40/30* (2020.01)
*A24F 40/485* (2020.01)
*A24F 7/00* (2006.01)
*H05B 3/44* (2006.01)
*A61M 11/04* (2006.01)
*A24F 40/10* (2020.01)
*A24F 40/20* (2020.01)
*A24D 3/04* (2006.01)

(52) U.S. Cl.
CPC .......... *A61M 15/0021* (2014.02); *H05B 3/44* (2013.01); *A24D 3/043* (2013.01); *A24F 40/10* (2020.01); *A24F 40/20* (2020.01); *A61M 11/042* (2014.02); *A61M 2205/3334* (2013.01); *A61M 2205/3653* (2013.01); *A61M 2205/8212* (2013.01)

(56) References Cited

U.S. PATENT DOCUMENTS

| | | |
|---|---|---|
| D624,238 S | 9/2010 | Turner |
| 8,205,622 B2 | 6/2012 | Pan |
| 8,746,240 B2 | 6/2014 | Terry et al. |
| 9,072,321 B2 | 7/2015 | Liu |
| 9,271,527 B2 | 3/2016 | Liu |
| 9,538,788 B2 | 1/2017 | Cyphert et al. |
| 9,668,522 B2 | 6/2017 | Memari et al. |
| 2008/0053465 A1 | 3/2008 | Tarora et al. |
| 2013/0192619 A1 | 8/2013 | Tucker et al. |
| 2013/0192623 A1 | 8/2013 | Tucker et al. |
| 2014/0000638 A1 | 1/2014 | Sebastian et al. |
| 2014/0261488 A1 | 9/2014 | Tucker |
| 2014/0334802 A1 | 11/2014 | Dubief |
| 2014/0366898 A1 | 12/2014 | Monsees et al. |
| 2015/0047662 A1 | 2/2015 | Hopps |
| 2015/0164141 A1 | 6/2015 | Newton |
| 2015/0164145 A1 | 6/2015 | Zhou |
| 2015/0196060 A1 | 7/2015 | Wensley et al. |
| 2015/0305410 A1 | 10/2015 | Liu |
| 2016/0213065 A1 | 7/2016 | Wensley et al. |
| 2016/0219932 A1 | 8/2016 | Glaser |
| 2016/0262456 A1 | 9/2016 | Borkovec et al. |
| 2016/0331026 A1 | 11/2016 | Cameron |
| 2017/0105453 A1 | 4/2017 | Ll et al. |
| 2017/0119056 A1 | 5/2017 | Liu |
| 2017/0251721 A1 | 9/2017 | Rostami et al. |
| 2017/0258138 A1 | 9/2017 | Rostami et al. |
| 2018/0027882 A1* | 2/2018 | Hepworth ............... A24F 40/42 |
| 2018/0049477 A1 | 2/2018 | Suzuki et al. |
| 2019/0183177 A1 | 6/2019 | Hubbard et al. |
| 2019/0183183 A1 | 6/2019 | Ito |

FOREIGN PATENT DOCUMENTS

| | | |
|---|---|---|
| CN | 105357991 A | 2/2016 |
| CN | 106376973 A | 2/2017 |
| CN | 106388006 A | 2/2017 |
| CN | 106723358 A | 5/2017 |
| EP | 2961285 A2 | 1/2016 |
| JP | 2016-511640 A | 4/2016 |
| JP | 2016-535982 A | 11/2016 |
| RU | 2602962 C2 | 11/2016 |
| RU | 2626933 C2 | 8/2017 |
| WO | WO-2015/052192 A1 | 4/2015 |
| WO | WO-2016/178377 A1 | 11/2016 |
| WO | WO-2017046566 A1 | 3/2017 |
| WO | WO-2018/130391 A1 | 7/2018 |

OTHER PUBLICATIONS

Russian Office Action for corresponding Application No. 2020121874, dated Dec. 29, 2021, English translation included herewith.
Russian Decision to Grant for corresponding Application No. 2020121874, dated May 6, 2022, with English translation.
European Office Action for corresponding Application No. 18829885.5, dated Jun. 23, 2021.
Brazilian Office Action for corresponding Application No. 112020011058-2, dated Jul. 21, 2022, with English Translation.
www.e-cigarette-forum.com/forum/threads/basic-design-flaw.55467/ > last accessed Dec. 29, 2017.
International Search Report and Written Opinion thereof dated Feb. 20, 2019 for corresponding International Application No. PCT/EP2018/086855.
International Preliminary Report on Patentability dated Nov. 19, 2019 for corresponding International Application No. PCT/EP2018/086855.
Japanese Office Action for corresponding Application No. 2020-534825, dated Jan. 12, 2023, with English Translation.
Chinese Office Action for corresponding Application No. 201880078733.3, dated Feb. 10, 2023, English translation included.
Japanese Notice of Allowance for corresponding Application No. 2020-534825, dated Mar. 30, 2023, with English Translation.

* cited by examiner

TIP DEVICE FOR ELECTRONIC VAPING DEVICE

CROSS-REFERENCE TO RELATED APPLICATIONS

The present application is a continuation of U.S. application Ser. No. 15/858,546, filed on Dec. 29, 2017, the entire contents of which are incorporated herein by reference.

BACKGROUND

Field

The present disclosure relates to electronic vaping and/or e-vaping devices.

Description of Related Art

E-vaping devices, also referred to herein as electronic vaping devices (EVDs) may be used by adult vapers for portable vaping. Mixed vapors within an e-vaping device may be used to deliver a flavor along with the vapor that may be produced by the e-vaping device. The mixed vapors may be delivered via a flavor system.

In some cases, a change of flavoring in a mixed vapor may occur as a result of chemical reactions between a pre-vapor formulation that is used to generate a generated vapor and one or more additive materials configured to release additives (e.g., a flavor material configured to release a flavorant) into a generated vapor to form the mixed vapor.

A change of flavoring may include a loss of flavoring in the mixed vapor, where the loss of flavoring may occur as a result of chemical reactions between the pre-vapor formulation and one or more additive materials. Such a loss of flavoring may reduce a sensory experience provided by the e-vaping device.

SUMMARY

According to some example embodiments, a tip device for an electronic vaping device (EVD) may include a first conduit structure and a second conduit structure. The first conduit structure may have a surface at least partially defining a first conduit having an inlet end and an opposite outlet end. The first conduit structure may be configured to receive a generated vapor from an external source via the inlet end of the first conduit and direct the received generated vapor through the first conduit towards the outlet end of the first conduit. The second conduit structure may have a surface at least partially defining a second conduit having an inlet end and an opposite outlet end. The second conduit structure may be configured to receive an air flow from an ambient environment via the inlet end of the second conduit and direct the air flow through the second conduit towards the outlet end of the second conduit. The second conduit structure may include an additive material on a surface of the second conduit structure. The additive material may include an additive. The additive material may be configured to release the additive into the air flow directed through the second conduit. At least an interposing structure of the first conduit structure and the second conduit structure may physically isolate the additive material from the first conduit, such that the additive material is configured to release the additive into the air flow directed through the second conduit independently of the generated vapor directed through the first conduit.

The tip device may further include an outlet assembly configured to receive the air flow and the generated vapor from the respective outlet ends of the first and second conduits, mix the air flow and the generated vapor to establish a mixed vapor, and direct the mixed vapor out of the tip device.

The interposing structure may be common to both the first conduit structure and the second conduit structure, such that the interposing structure at least partially defines both the first conduit and the second conduit.

The interposing structure may include opposite surfaces at least partially defining separate conduits of the first conduit and the second conduit.

The interposing structure may include a hollow cylindrical structure having an inner surface and an outer surface extending along a longitudinal axis. The first conduit may be a cylindrical conduit. The second conduit may be an annular conduit surrounding the first conduit and extending coaxially with the first conduit along the longitudinal axis, the second conduit at least partially defined by at least the outer surface of the interposing structure.

The additive material may be on the outer surface of the interposing structure.

The tip device may further include an additional additive assembly in fluid communication with the first conduit. The additional additive assembly may be configured to release an additional additive into the generated vapor that is directed through the first conduit, such that the air flow directed through the outlet end of the second conduit includes the additive, and the generated vapor directed through the outlet end of the first conduit includes the additional additive.

The additive material may include an adsorbent material.

The tip device may further include an adjustable flow control assembly coupled to the inlet end of the second conduit. The adjustable flow control assembly may be configured to adjustably control an effective cross-sectional flow area of the inlet end to control a flow rate of air drawn into the second conduit via the inlet end of the second conduit.

According to some example embodiments, an e-vaping device may include a vaporizer assembly configured to form a generated vapor and a tip device in fluid communication with the vaporizer assembly. The tip device may include a first conduit structure and a second conduit structure. The first conduit structure may have a surface at least partially defining a first conduit having an inlet end and an opposite outlet end. The first conduit structure may be configured to receive the generated vapor from the vaporizer assembly via the inlet end of the first conduit and direct the received generated vapor through the first conduit towards the outlet end of the first conduit. The second conduit structure may have a surface at least partially defining a second conduit having an inlet end and an opposite outlet end. The second conduit structure may be configured to receive an air flow from an ambient environment via the inlet end of the second conduit and direct the air flow through the second conduit towards the outlet end of the second conduit. The second conduit structure may include an additive material on a surface of the second conduit structure. The additive material may include an additive. The additive material may be configured to release the additive into the air flow directed through the second conduit. At least an interposing structure of the first conduit structure and the second conduit structure may physically isolate the additive material from the first conduit, such that the additive material is configured to release the additive into the air flow directed through the second conduit independently of the generated vapor directed through the first conduit. The e-vaping device may further include a power supply section configured to supply power to the vaporizer assembly.

The e-vaping device may further include an outlet assembly configured to receive the air flow and the generated vapor from the respective outlet ends of the first and second conduits, mix the air flow and the generated vapor to establish a mixed vapor, and direct the mixed vapor out of the tip device.

The interposing structure may be common to both the first conduit structure and the second conduit structure, such that the interposing structure at least partially defines both the first conduit and the second conduit.

The interposing structure may include opposite surfaces defining separate conduits of the first conduit and the second conduit.

The interposing structure may include a hollow cylindrical structure having an inner surface and an outer surface extending along a longitudinal axis. The first conduit may be a cylindrical conduit, and the second conduit may be an annular conduit surrounding the first conduit and extending coaxially with the first conduit along the longitudinal axis, the second conduit at least partially defined by at least the outer surface of the interposing structure.

The additive material may be on the outer surface of the interposing structure.

The tip device may further include an additional additive structure in fluid communication with the first conduit. The additional additive structure may be configured to release an additional additive into the generated vapor that is directed through the first conduit, such that the air flow directed through the outlet end of the second conduit includes the additive, and the generated vapor directed through the outlet end of the first conduit includes the additional additive.

The additive material may include an adsorbent material.

The power supply section may include a rechargeable battery.

The tip device may be reversibly coupled to the vaporizer assembly.

The tip device may further include an adjustable flow control assembly coupled to the inlet end of the second conduit, the adjustable flow control assembly configured to adjustably control an effective cross-sectional flow area of the inlet end to control a flow rate of air drawn into the second conduit via the inlet end of the second conduit.

According to some example embodiments, a method of operation of a tip device, where the tip device is configured to be reversibly coupled to an external source and the external source is configured to generate a generated vapor, may include: receiving, at an inlet end of a first conduit at least partially defined by a first conduit structure, the generated vapor from the external source, directing the received generated vapor through the first conduit towards an opposite outlet end of the first conduit, receiving, at an inlet end of a separate second conduit at least partially defined by a second conduit structure, an air flow from an ambient environment, directing the air flow through the second conduit in fluid communication with an additive material on a surface of the second conduit, such that an additive is released from the additive material into the air flow independently of the generated vapor directed through the first conduit, and further directing the air flow through the second conduit towards an opposite outlet end of the second conduit, wherein an interposing structure of the tip device physically isolates the additive material from the first conduit, such that the additive material releases the additive into the air flow directed through the second conduit independently of the generated vapor directed through the first conduit, and directing the generated vapor directed out of the outlet end of the first conduit and the air flow directed out of the outlet end of the second conduit through a common conduit, such that the generated vapor and the air flow mix to form a mixed vapor.

The interposing structure may include opposite surfaces defining separate conduits of the first conduit and the second conduit.

The interposing structure may include a hollow cylindrical structure having an inner surface and an outer surface extending along a longitudinal axis, the first conduit may be a cylindrical conduit, and the second conduit may be an annular conduit surrounding the first conduit and extending coaxially with the first conduit along the longitudinal axis, the second conduit at least partially defined by at least the outer surface of the interposing structure.

The additive material may be on the outer surface of the interposing structure.

The method may further include directing the generated vapor in fluid communication with an additional additive assembly, such that the additional additive assembly releases an additional additive into the generated vapor that is directed through the first conduit, the air flow directed through the outlet end of the second conduit includes the additive, and the generated vapor directed through the outlet end of the first conduit includes the additional additive.

The additive material may include an adsorbent material.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims.

The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1A:
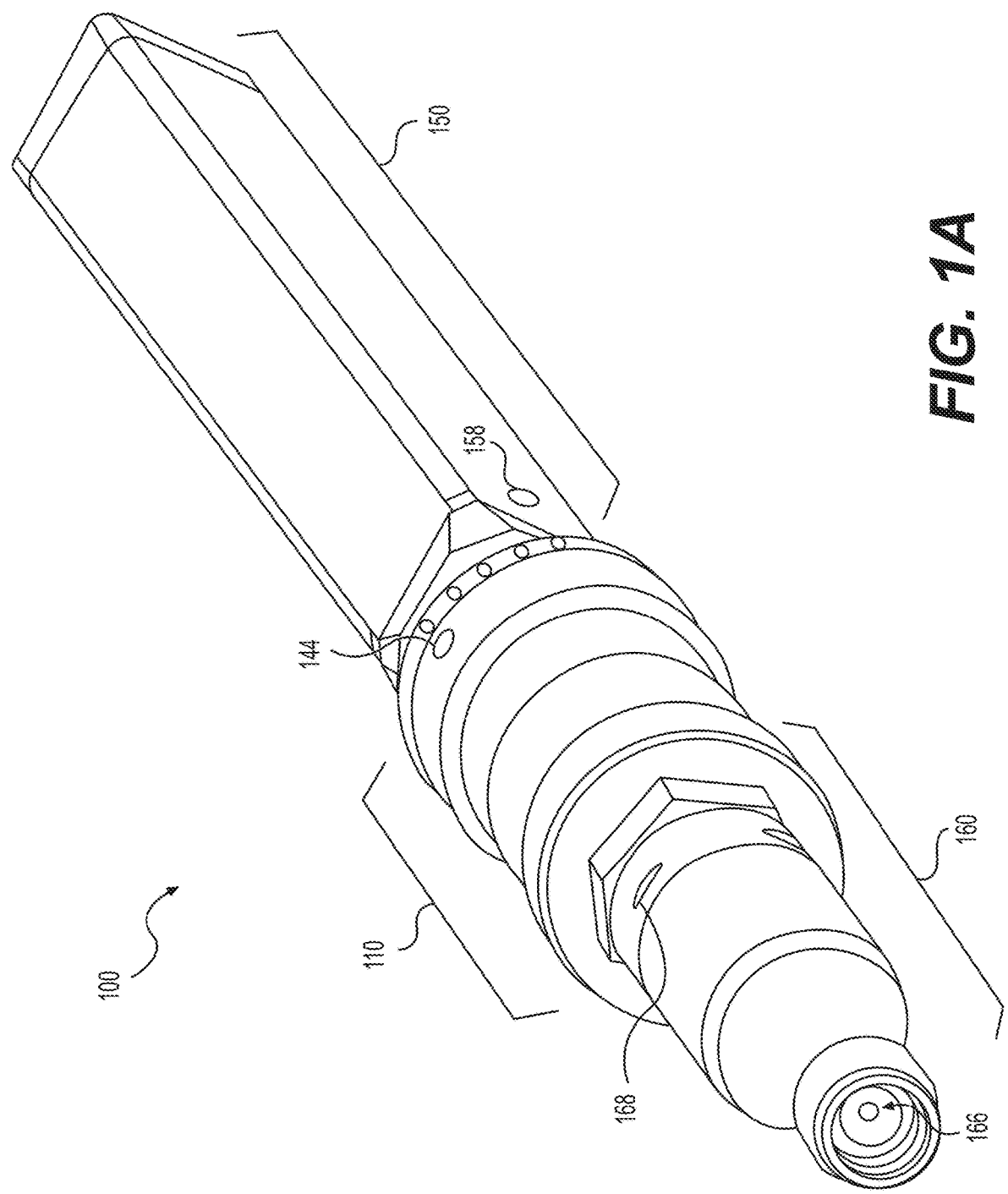
FIG. 1A is a perspective view of an e-vaping device according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

E-Vaping Device

Figure 1B:
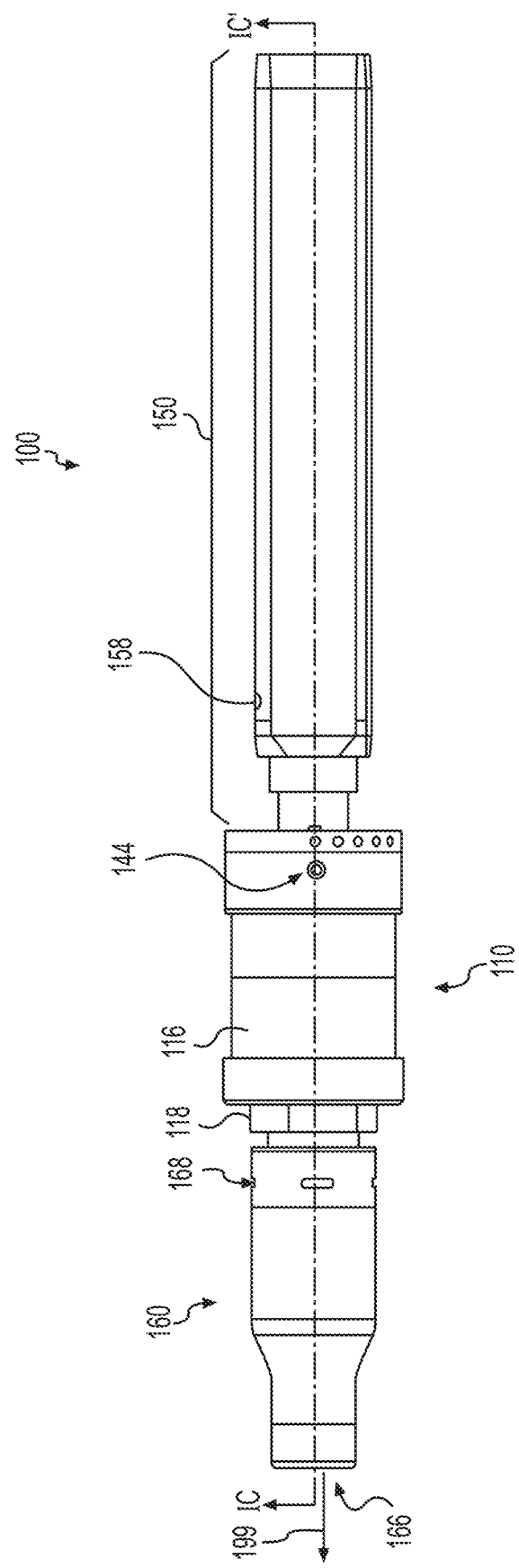
FIG. 1B is a plan side view of the e-vaping device of FIG. 1A.
Figure 1C:
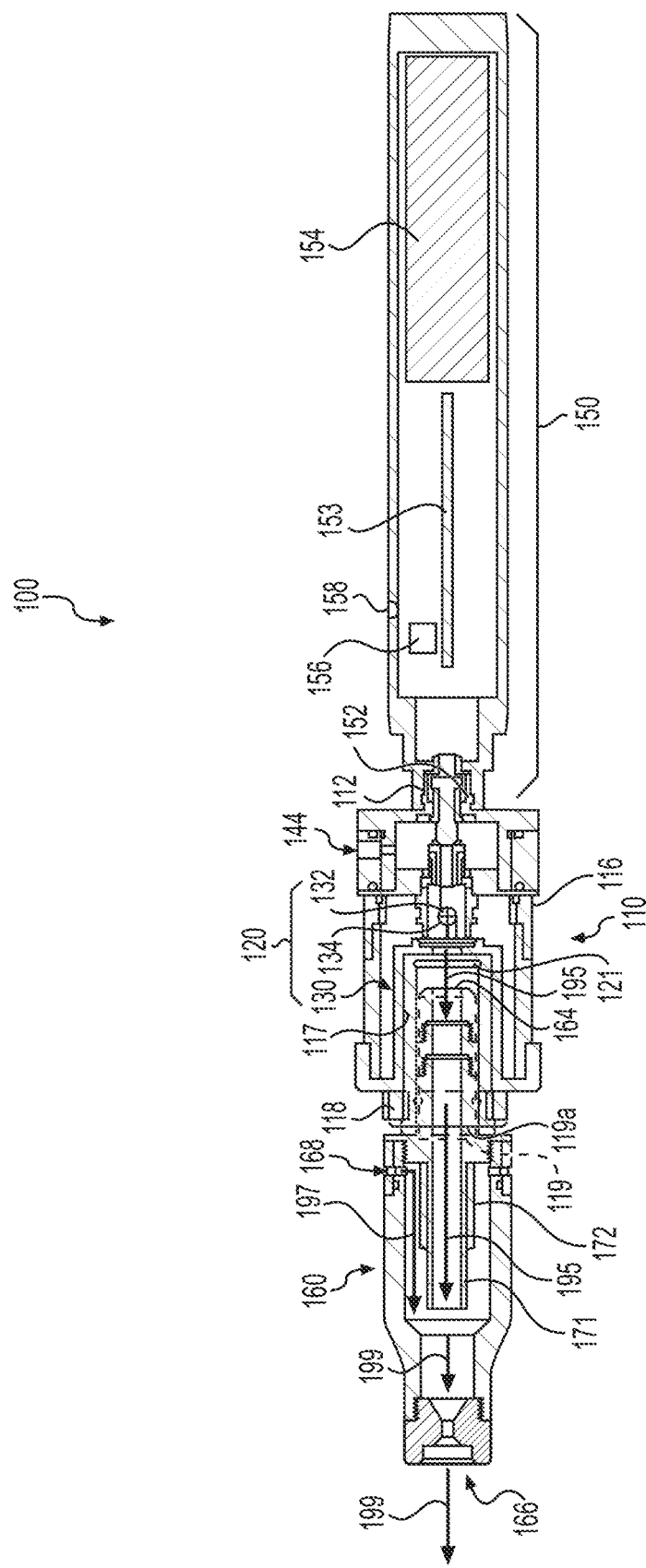
FIG. 1C is a cross-sectional view along line IC-IC' of the e-vaping device of FIG. 1B.
Figure 2A:
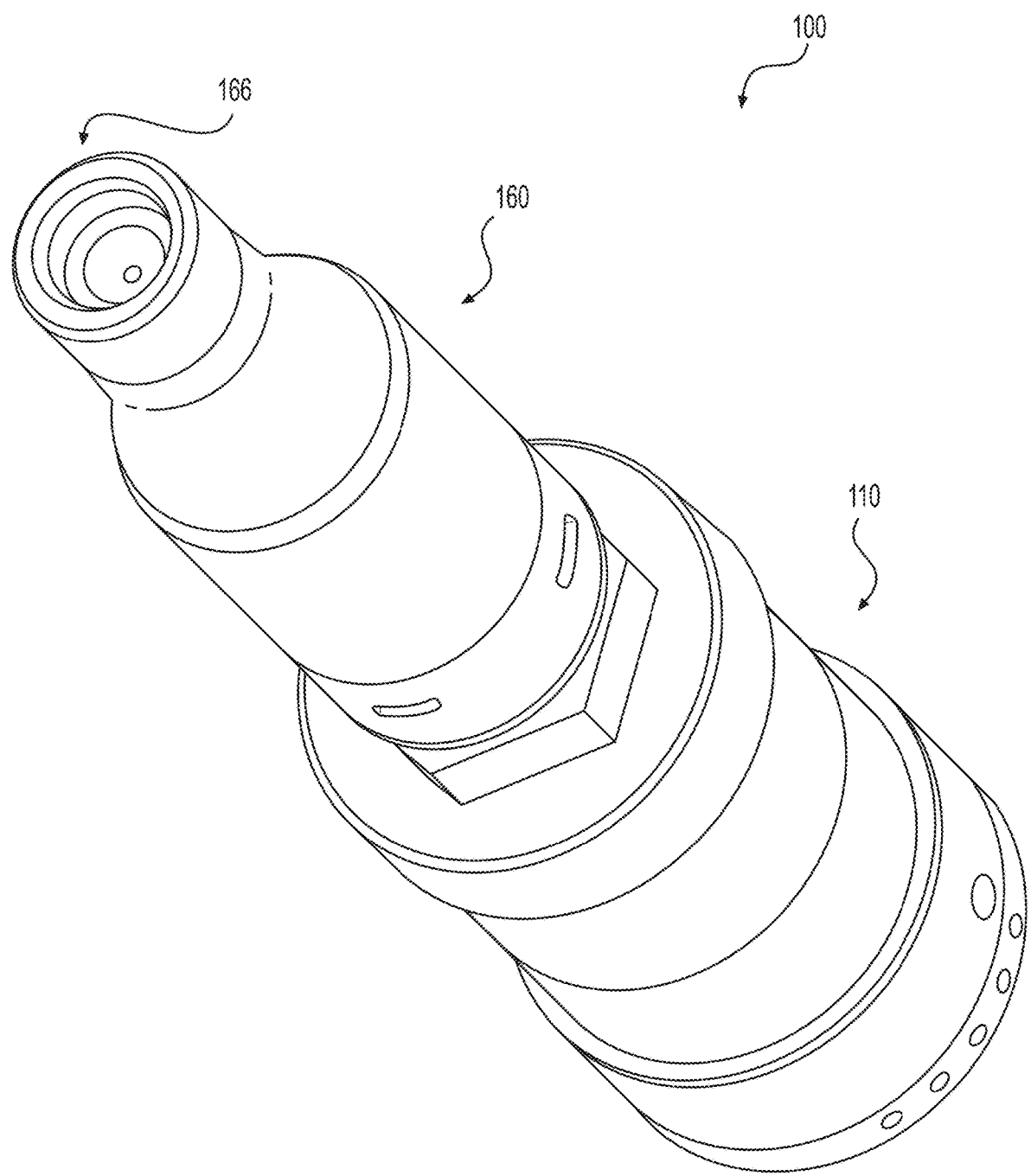
FIG. 2A is a perspective view of an e-vaping device according to some example embodiments.
Figure 2B:
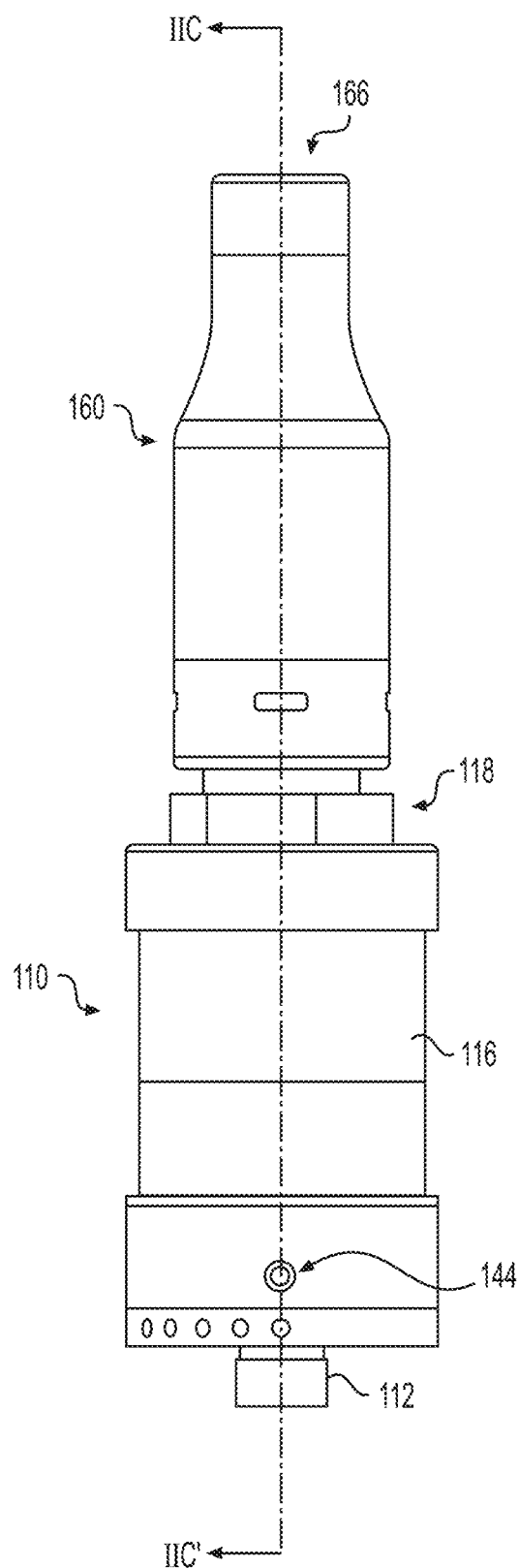
FIG. 2B is a plan side view of the e-vaping device of FIG. 2A.
Figure 2C:
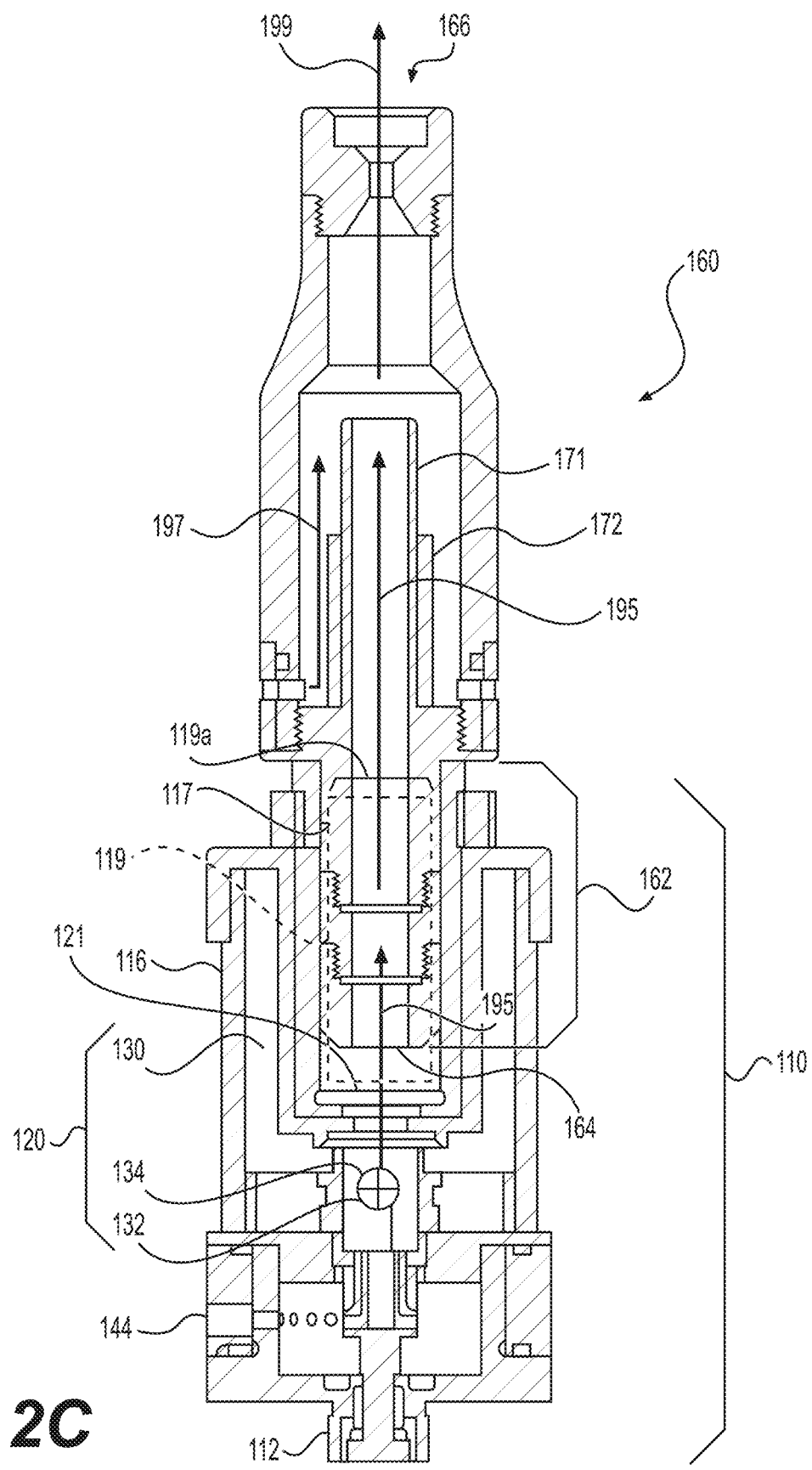
FIG. 2C is a plan cross-sectional view of the e-vaping device of FIG. 2B along cross-sectional view line IIC-IIC', according to some example embodiments.

FIG. 1A is a perspective view of an e-vaping device according to some example embodiments. FIG. 1B is a plan side view of the e-vaping device of FIG. 1A. FIG. 1C is a cross-sectional view along line IC-IC' of the e-vaping device of FIG. 1B. FIG. 2A is a perspective view of an e-vaping device according to some example embodiments. FIG. 2B is a plan side view of the e-vaping device of FIG. 2A. FIG. 2C is a plan cross-sectional view of the e-vaping device of FIG. 2B along cross-sectional view line IIC-IIC', according to some example embodiments.

The e-vaping device 100 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of each of which are incorporated herein by reference thereto. As used herein, the term "e-vaping device" is inclusive of all types of electronic vaping devices, regardless of form, size or shape.

Referring to FIGS. 1A-1C, an e-vaping device 100 may include at least one section of a replaceable cartridge (or first section) 110 and a reusable power supply section (or second section) 150. The sections 110, 150 may be reversibly or irreversibly coupled together at complementary interfaces 112, 152 of the respective sections 110, 150. As described further below, the cartridge 110 is configured to generate a generated vapor 195 based at least in part upon electrical power supplied from the power supply section 150. In some example embodiments, the interfaces 112, 152 are threaded connectors. It should be appreciated that an interface 112, 152 may be any type of connector, including, without limitation, a snug-fit, detent, clamp, bayonet, and/or clasp.

Referring to FIGS. 1A-2C, the e-vaping device 100 may include a tip device (or third section) 160 configured to be reversibly or irreversibly coupled to the cartridge 110 so that the tip device 160 is configured to receive an entirety or substantial entirety (e.g., an entirety within manufacturing tolerances and/or material tolerances) of the generated vapor 195 from the cartridge 110. The sections 160, 110 may be coupled together at complementary interfaces 162, 118 of the respective sections 160, 110. As described further below, the complementary interfaces 162, 118 may be configured to establish an airtight or substantially airtight (e.g., airtight within manufacturing tolerances and/or material tolerances) seal between the sections 160, 110, so that the tip device 160 is configured to receive the entirety or substantial entirety of the generated vapor 195 from the cartridge 110 via the outlet port 121 of the cartridge 110.

As described further below, the tip device 160 is configured to mix the generated vapor 195 with one or more additives (e.g., a flavorant) to form a mixed vapor 199 (e.g., a "flavored vapor") and to further direct the mixed vapor 199 out of the e-vaping device 100 via outlet 166 of the tip device 160, thereby configuring the e-vaping device 100 to provide a mixed vapor 199 while reducing or minimizing the interaction between the additive and pre-vapor formulation prior to the generation of the generated vapor 195, thereby improving the ability of the e-vaping device 100 to provide a more consistent and reliable sensory experience through the mitigation of various chemical reactions between the additive and the pre-vapor formulation within the e-vaping device 100.

As shown in FIG. 1A-2C, in some example embodiments, the cartridge 110 includes a vaporizer assembly 120 that is configured to generate a generated vapor 195. As illustrated, the vaporizer assembly 120 may include a reservoir 130 configured to hold a pre-vapor formulation, a dispensing interface 132 configured to draw pre-vapor formulation from the reservoir 130, and a heating element 134 configured to vaporize the drawn pre-vapor formulation to form the generated vapor 195. As further shown, the cartridge 110 includes one or more air inlet ports 144 through which ambient air may be drawn into the cartridge 110 to flow in fluid communication with the vaporizer assembly 120, particularly the dispensing interface 132, towards the outlet 121 of the cartridge 110.

In some example embodiments, the cartridge 110 may include at least one air inlet port 144 that may be formed in the outer housing 116 of the cartridge 110, adjacent to the interface 112 to reduce and/or minimize the probability of an adult vaper's fingers occluding one of the ports and to control the resistance-to-draw (RTD) during vaping. In some example embodiments, the air inlet ports 144 may be machined into the outer housing 116 with precision tooling such that their diameters are closely controlled and replicated from one e-vaping device 100 to the next during manufacture.

In some example embodiments, the air inlet ports 144 may be drilled with carbide drill bits or other high-precision tools and/or techniques. In some example embodiments, the outer housing 116 may be formed of metal or metal alloys such that the size and shape of the air inlet ports 144 may not be altered during manufacturing operations, packaging, and vaping. Thus, the air inlet ports 144 may provide consistent RTD. In some example embodiments, the air inlet ports 144 may be sized and configured such that the e-vaping device 100 has a RTD in the range of from about 60 mm $H_2O$ to about 150 mm $H_2O$.

Still referring to FIGS. 1A-2C, the reservoir 130 may include a pre-vapor formulation. The reservoir 130 may be at least partially defined by one or more structural elements of the cartridge 110, including the outer housing 116 as illustrated, such that the reservoir 130 may be contained in an outer annulus structure. Thus, for example, the reservoir 130 may at least partially surround the cavity 119 defined by the inner surface 117 of the outlet interface 118, as described below.

The dispensing interface 132 is coupled to the reservoir 130. The dispensing interface 132 is configured to draw pre-vapor formulation from the reservoir 130. The heating element 134 is coupled to the dispensing interface 132 and is configured to generate heat. The dispensing interface 132 is configured to draw pre-vapor formulation from the reservoir 130, such that the pre-vapor formulation may be vaporized from the dispensing interface 132 based on heating of the dispensing interface 132 by the heating element 134.

During vaping, pre-vapor formulation may be transferred from the reservoir 130 and/or storage medium in the proximity of the heating element 134 via capillary action of a dispensing interface 132. The dispensing interface 132 may include a first end portion and a second end portion. The first and second end portions of the dispensing interface 132 may extend into opposite sides of the reservoir 130. Dispensing interface 132 end portions may be referred to herein as roots. The heating element 134 may at least partially surround a central portion of the dispensing interface 132 such that if and/or when the heating element 134 is activated to generate heat, the pre-vapor formulation in the central portion of the dispensing interface 132 may be vaporized by the heating element 134 to form a generated vapor 195. The central portion of a dispensing interface 132 may be referred to herein as a trunk.

Furthermore, during vaping, air (sometimes referred to herein as a "first air flow") may be drawn into the cartridge 110, and into fluid communication with the dispensing interface 132, from an ambient environment via the one or more air inlet ports 144. The generated vapor 195 that is generated based on the heating element 134 heating the pre-vapor formulation drawn into the dispensing interface 132 may be entrained in the air drawn into the cartridge 110, and the resulting generated vapor 195 may be drawn out of the cartridge 110 with the first air flow via the outlet port 121.

The reservoir 130 may include a pre-vapor formulation which is free of additives, such that if and/or when the vaporizer assembly 120 forms a generated vapor 195, via vaporization of a pre-vapor formulation by the heating element 134, the generated vapor 195 may be absent or substantially absent (e.g., absent within manufacturing tolerances and/or material tolerances) of various additives, including flavorants. Such an absence of additives in the reservoir 130 of the vaporizer assembly 120 may result in mitigation of chemical reactions between pre-vapor formulation materials and additives, including flavorants, in the reservoir 130 and upon vaporization as a result of heating of the pre-vapor formulation by the heating element 134.

As described further below, the one or more elements of the generated vapor 195 may include one or more elements of a pre-vapor formulation from which the generated vapor 195 is formed. The one or more elements may include at least one of water, solvents, active ingredients, ethanol, plant extracts, and natural or artificial flavors. A pre-vapor formulation may include at least one of glycerin and propylene glycol.

As shown in FIG. 1A-2C, in some example embodiments, the e-vaping device 100 may include a tip device 160 that may form a mixed vapor 199 based on mixing the generated vapor 195 with an additive. As described further below, the tip device 160 may release the additive into an air flow 197 (sometimes referred to herein as a "second air flow") that is separate from the generated vapor 195 and is drawn into the tip device 160 separately from the generated vapor 195 (e.g., release the additive into an air flow 197 independently of the generated vapor 195) via a separate air inlet 168. The tip device 160 may mix the air flow 197 into which the additive has been released with the generated vapor 195 to form the mixed vapor 199.

As further described below, the tip device 160 holds an additive material 172 in fluid communication with a conduit that is physically isolated from a conduit configured to receive the generated vapor 195 from the cartridge 110, such that pre-vapor generation interactions between the additive held in the additive material 172 and a pre-vapor formulation held in the vaporizer assembly 120 is reduced and/or minimized. As a result, a loss of flavor in the mixed vapor 199 that may result from such interactions may be reduced and/or mitigated. Thus, the e-vaping device 100 is configured to generate a mixed vapor 199 that provides an improved sensory experience, based on being configured to reduce and/or mitigate interactions between the additive material 172 and the vaporizer assembly 120 via physical isolation of the additive material 172 from the conduit of the tip device 160 that is configured to receive the generated vapor 195 from the cartridge 110 in which the vaporizer assembly 120 is included.

In some example embodiments, the tip device 160 may include at least an interposing structure 171 that physically isolates an additive material 172, configured to release the additive into the air flow 197, from a separate conduit configured to receive and direct the generated vapor 195 to an outlet end of the separate conduit. As a result, the generated vapor 195 and the air flow 197 may be mixed subsequent to an additive being released into the air flow 197, so that the resulting mixture (referred to herein as the "mixed vapor" 199) may include the generated vapor 195 and the additive. The additive may include a flavorant. In some example embodiments, the additive may include nicotine. In some example embodiments, the tip device 160 is configured to release an additional additive into the generated vapor 195 separately from the additive being released into the air flow 197. As a result, in some example embodiments, including the example embodiments shown in FIGS. 1A-2C, the air flow 197, including an additive (also referred to herein as a "first additive"), may be mixed with the generated vapor 195, including an additional additive (also referred to herein as a "second additive"), to form a mixed vapor 199 that includes both the first additive and the second additive. In some example embodiments, the first additive includes nicotine, and the second additive includes a flavorant and does not include nicotine.

In some example embodiments, the additive material 172 of the tip device 160 may include an adsorbent material that is configured to release one or more additives into the air flow 197 based on desorption of the one or more additives from the adsorbent material. The additive may be desorbed from the additive material 172 based on one or more elements of the air flow 197 adsorbing on the one or more adsorbent materials, thereby displacing the one or more additives on the one or more adsorbent materials. In some example embodiments, the additive material 172 is configured to react with one or more elements of the air flow 197 to release the one or more additives. In some example embodiments, the additive material 172 holds an additive that includes a volatile compound, such that the additive material 172 is configured to release the additive into an air flow 197 that passes in flow communication with the additive material 172.

In some example embodiments, the additive material 172 of the tip device 160 may be configured to release one or more additives at one or more particular release rates. In some example embodiments, a tip device 160 includes an additive material 172 that is configured to release an additive at a particular release rate based on air flow 197 passing in fluid communication with the additive material 172. For example, an additive material 172 may be configured to release an additive at a relatively rapid rate (e.g., "quick release") based on air flow 197 passing in fluid communication with the additive material 172, such that the tip device 160 is configured to provide a short-term sensory experience via mixed vapor 199. In another example, an additive material 172 may be configured to release an additive at a relatively slow rate (e.g., "slow release") based on air flow 197 passing in fluid communication with the additive material 172, such that the tip device 160 may be configured to have a relatively long storage life. In some example embodiments, where the additive material 172 is configured to release multiple separate additives from a common additive material, the additive material 172 may be configured to release the separate additives at separate, different, respective release rates based on air flow 197 passing in fluid communication with the additive material 172. In some example embodiments, the additive material 172 may include multiple separate materials that are configured to release one or more additives at separate, different, respective release rates.

Referring back to the cartridge 110, and as shown in FIG. 1A-2C, in some example embodiments, the outlet interface 118 of the cartridge 110 includes at least one outlet port 121 and an inner surface 117 that defines a cylindrical cavity 119 with the outlet port 121 at one end of the cavity and an opening 119a at an opposite end of the cavity 119. As shown in FIGS. 1A-2C, the outlet interface 118 is configured to couple with an inlet interface 162 of the tip device 160 to establish an airtight or substantially airtight seal (e.g., an airtight seal within manufacturing tolerances and/or material tolerances) between the inlet 164 of the tip device 160 and the outlet port 121 of the cartridge 110, thereby enabling the cartridge 110 to direct a generated vapor 195 that is generated by the vaporizer assembly 120 to flow entirely or substantially entirely (e.g., entirely within manufacturing tolerances and/or material tolerances) from the cartridge 110 into the tip device 160.

As shown in FIGS. 1A-2C, the inner surface 117 of the outlet interface 118 of the cartridge 110 at least partially defines a cavity 119, such that the outlet interface 118 is configured to receive the inlet interface 162 of the tip device 160 into the cavity 119 via the opening 119a. As a result, if and/or when an inlet interface 162 of a tip device 160 is inserted into the cavity 119 of the outlet interface 118 via opening 119a to couple the tip device 160 with the cartridge 110, an inlet 164 of the tip device 160 that is included in the interface 162 may be positioned proximate to and in fluid communication with the outlet port 121 of the cartridge 110, such that the tip device 160 is configured to receive the generated vapor 195 generated by the vaporizer assembly 120 from the outlet port 121 via the inlet 164 of the tip device 160.

Referring back to FIGS. 1A-1C, the power supply section 150 includes a sensor 156 responsive to air drawn into the power supply section 150 via an air inlet port 158 adjacent to a free end or tip end of the e-vaping device 100, at least one power supply 154, and control circuitry 153. The power supply 154 may include a rechargeable battery. The sensor 156 may be one or more of a pressure sensor, a microelectromechanical system (MEMS) sensor, etc.

The sensor 156 may be configured to generate an output indicative of a magnitude and direction of airflow (flowing through the vaporizer assembly 120), where the control circuitry 153 receives the sensor 156 output and determines if the following 'vaping conditions' exist: (1) a direction of the airflow indicates a draw on the outlet 166 (versus air entering the e-vaping device 100 through the outlet 166), and (2) a magnitude of the airflow exceeds a threshold value. If these internal vaping conditions of the e-vaping device 100 are met, the control circuitry 153 may electrically connect the power supply 154 to the cartridge 110 and the vaporizer assembly 120, thereby activating both the cartridge 110 and the vaporizer assembly 120. In some example embodiments, the sensor 156 may generate an output indicative of a pressure drop within the housing of the e-vaping device 100 (which is caused by a draw of air entering the power supply section 150 through an air inlet port 158, and exiting the e-vaping device 100 through the outlet 166), whereupon the control circuitry 153 activates the cartridge 110 and the vaporizer assembly 120, in response thereto. The sensor 156 may be a sensor as disclosed in U.S. application Ser. No. 14/793,453, filed on Jul. 7, 2015 and published as U.S. Publication No. 2015/0305410, or a sensor as disclosed in U.S. Pat. No. 9,072,321, issued on Jul. 7, 2015, each of which is hereby incorporated by reference in their entirety into this document.

In some example embodiments, one or more of the interfaces 112, 152 include one or more of a cathode connector element and an anode connector element. The power supply section 150 may include one or more leads (not shown) that couple control circuitry 153 and/or power supply 154 to the interface 152. If and/or when interfaces 112, 152 are coupled together, the coupled interfaces 112, 152 may electrically couple the control circuitry 153, power supply 154, and/or vaporizer assembly 120 together.

The power supply 154 may be a Lithium-ion battery or one of its variants, for example a Lithium-ion polymer battery. Alternatively, the power supply 154 may be a nickel-metal hydride battery, a nickel cadmium battery, a lithium-manganese battery, a lithium-cobalt battery or a fuel cell. The e-vaping device 100 may be usable by an adult vaper until the energy in the power supply 154 is depleted or in the case of lithium polymer battery, a minimum voltage cut-off level is achieved.

Further, the power supply 154 may be rechargeable and may include circuitry configured to allow the battery to be chargeable by an external charging device. To recharge the e-vaping device 100, a Universal Serial Bus (USB) charger or other suitable charger assembly may be used.

Upon the connection between the cartridge 110 and the power supply section 150 being completed, the at least one power supply 154 may be electrically connected with the heating element 134 of the cartridge 110 upon actuation of the sensor 156. Air is drawn primarily into the cartridge 110 through one or more air inlet ports 144. The one or more air inlet ports 144 may be located along the outer housing 116.

The sensor 156 may be configured to sense an air pressure drop and initiate application of voltage from the power supply 154 the heating element 134. Thus, the power supply section 150 may be configured to supply power to the vaporizer assembly 120.

In addition, the at least one air inlet port 158 may be located adjacent to the sensor 156, such that the sensor 156 may sense air flow indicative of vapor being drawn through the outlet end of the e-vaping device. The sensor 156 may activate the power supply 154.

Further, the control circuitry 153 may control the supply of electrical power to the heating element 134 responsive to the sensor 156. In some example embodiments, the control circuitry 153 may include a maximum, time-period limiter. In some example embodiments, the control circuitry 153 may include a manually operable switch for an adult vaper to manually initiate vaping. The time-period during which the control circuit 153 supplies the electric current to the heating element 134 may be pre-set depending on the amount of pre-vapor formulation desired to be vaporized. In some example embodiments, the control circuitry 153 may control the supply of electrical power to the heating element 134 as long as the sensor 156 detects a pressure drop.

To control the supply of electrical power to a heating element 134, the control circuitry 153 may execute one or more instances of computer-executable program code. The control circuitry 153 may include a processor and a memory. The memory may be a computer-readable storage medium storing computer-executable code.

The control circuitry 153 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 153 may be at least one of an application-specific integrated circuit (ASIC) and an ASIC chip.

The control circuitry 153 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The control circuitry 153 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The control circuitry 153 may be a special purpose machine configured to execute the computer-executable code to control the supply of electrical power to the heating element 134. Controlling the supply of electrical power to the heating element 134 may be referred to herein interchangeably as activating the heating element 134.

Still referring to FIGS. 1A-2C, if and/or when the heating element 134 is activated, the activated heating element 134 may heat a portion of a dispensing interface 132 surrounded by the heating element 134 for less than about 10 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

As described herein, the pre-vapor formulation is a material or combination of materials that may be transformed into a vapor. For example, the pre-vapor formulation may be a liquid, solid and/or gel formulation including, but not limited to, water, solvents, active ingredients, ethanol, plant extracts, natural or artificial flavors, and/or vapor formers such as glycerin and propylene glycol.

In some example embodiments, the pre-vapor formulation is one or more of propylene glycol, glycerin and combinations thereof.

The pre-vapor formulation may include nicotine or may exclude nicotine. The pre-vapor formulation may include one or more tobacco flavors. The pre-vapor formulation may include one or more flavors which are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid, sulfuric acid and combinations thereof.

In some example embodiments, a generated vapor 195 formed at the vaporizer assembly 120 may be substantially free of one or more materials being in a gas phase. For example, the generated vapor 195 may include one or more materials substantially in a particulate phase and substantially not in a gas phase.

The storage medium of the reservoir 130 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In some example embodiments, the reservoir 130 may include a filled tank lacking any storage medium and containing only pre-vapor formulation.

The reservoir 130 may be sized and configured to hold enough pre-vapor formulation such that the e-vaping device 100 may be configured for vaping for at least about 200 seconds. The e-vaping device 100 may be configured to allow each vaping to last a maximum of about 5 seconds.

The dispensing interface 132 may include a wick. The dispensing interface 132 may include filaments (or threads) having a capacity to draw the pre-vapor formulation. For example, a dispensing interface 132 may be a wick that is be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 100. In some example embodiments, the dispensing interface 132 may include one to eight filament strands, each strand comprising a plurality of glass filaments twisted together. The end portions of the dispensing interface 132 may be flexible and foldable into the confines of the reservoir 130. The filaments may have a cross-section that is generally cross-shaped, clover-shaped, Y-shaped, or in any other suitable shape.

The dispensing interface 132 may include any suitable material or combination of materials, also referred to herein as wicking materials. Examples of suitable materials may be, but not limited to, glass, ceramic- or graphite-based materials. The dispensing interface 132 may have any suitable capillary drawing action to accommodate pre-vapor formulations having different physical properties such as density, viscosity, surface tension and vapor pressure.

In some example embodiments, the heating element 134 may include a wire coil which at least partially surrounds the dispensing interface 132 in the vaporizer assembly 120. The wire may be a metal wire and/or the wire coil may extend fully or partially along the length of the dispensing interface. The wire coil may further extend fully or partially around the circumference of the dispensing interface 132. In some example embodiments, the wire coil may be isolated from direct contact with the dispensing interface 132.

The heating element 134 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 134 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 134 may include at least one material selected from the group consisting of stainless steel, copper, copper alloys, nickel-chromium alloys, super alloys and combinations thereof. In some example embodiments, the heating element 134 may be formed of nickel-chromium alloys or iron-chromium alloys. In some example embodiments, the heating element 134 may be a ceramic heater having an electrically resistive layer on an outside surface thereof.

The heating element 134 may heat a pre-vapor formulation in the dispensing interface 132 by thermal conduction. Alternatively, heat from the heating element 134 may be conducted to the pre-vapor formulation by means of a heat conductive element or the heating element 134 may transfer heat to the incoming ambient air that is drawn through the e-vaping device 100 during vaping, which in turn heats the pre-vapor formulation by convection.

It should be appreciated that, instead of using a dispensing interface 132, the vaporizer assembly 120 may include a heating element 134 that is a porous material which incorporates a resistance heater formed of a material having a high electrical resistance capable of generating heat quickly.

In some example embodiments, the cartridge 110 may be replaceable. In other words, once one of the flavorant or the pre-vapor formulation of the cartridge is depleted, only the cartridge 110 may be replaced. In some example embodiments, the entire e-vaping device 100 may be disposed once one of the reservoir 130 or the tip device 160 is depleted.

In some example embodiments, the e-vaping device 100 may be about 80 mm to about 110 mm long and about 7 mm to about 8 mm in diameter. For example, in some example embodiments, the e-vaping device 100 may be about 84 mm long and may have a diameter of about 7.8 mm.

As used herein, the term "additive" is used to describe a compound or combination of compounds that may provide a sensory experience to an adult vaper if and/or when the additive is included in a generated vapor. An additive may include a flavorant. In some example embodiments, an additive may include nicotine.

As used herein, the term "flavorant" is used to describe a compound or combination of compounds that may provide flavor and/or aroma to an adult vaper. In some example embodiments, a flavorant is configured to interact with sensory receptors that may be activated through orthonasal or retronasal paths of activation. A flavorant may include one or more volatile flavor substances.

The at least one flavorant may include one or more of a natural flavorant or an artificial ("synthetic") flavorant. The at least one flavorant may include one or more plant extracts. In some example embodiments, the at least one flavorant is one or more of tobacco flavor, menthol, wintergreen, peppermint, herb flavors, fruit flavors, nut flavors, liquor flavors, and combinations thereof. In some example embodiments, the flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material.

In some example embodiments, the tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, Dark Tobacco, rare tobacco, specialty tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

Tip Device

Figure 3A:
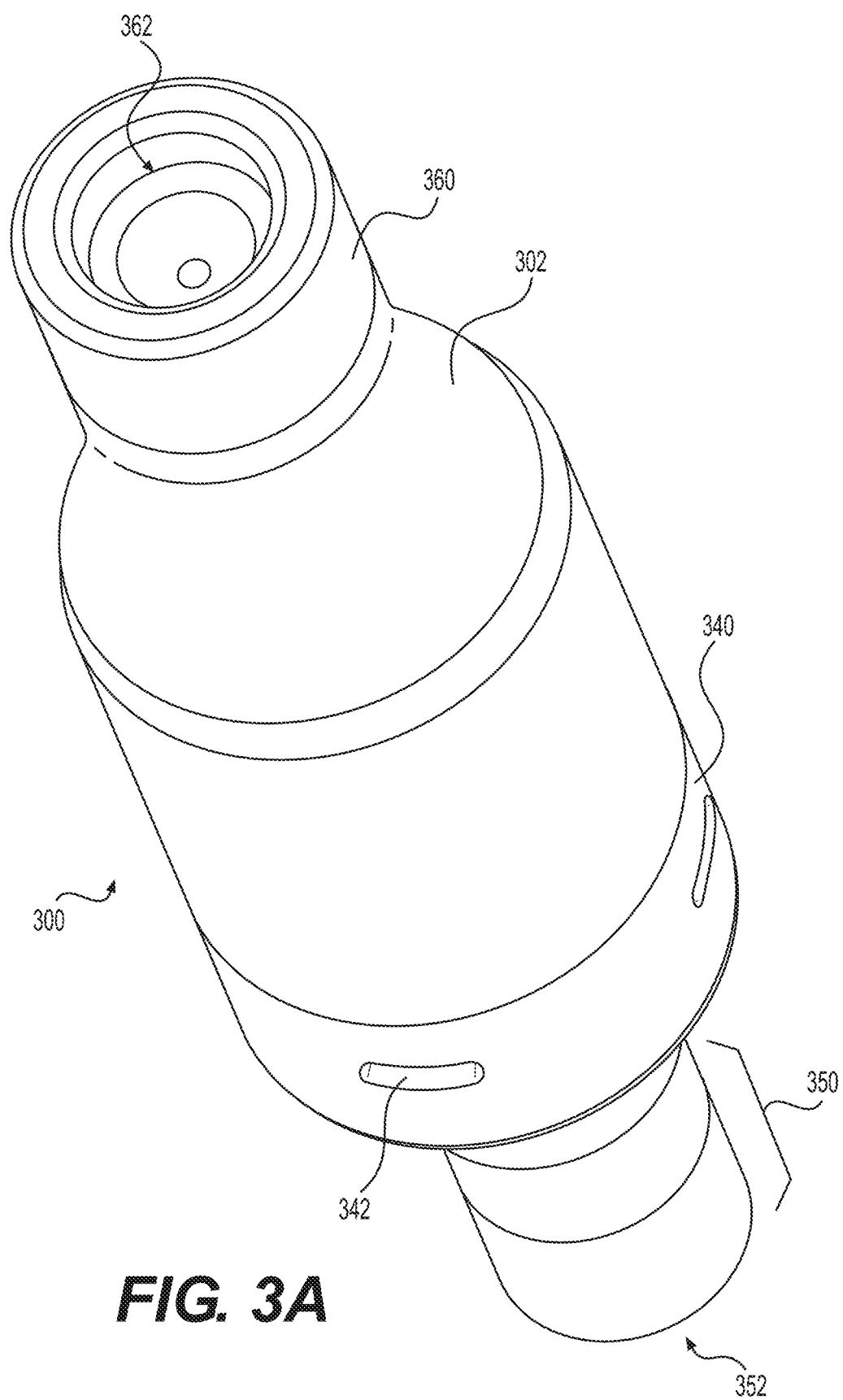
FIG. 3A is a perspective view of a tip device according to some example embodiments.
Figure 3B:
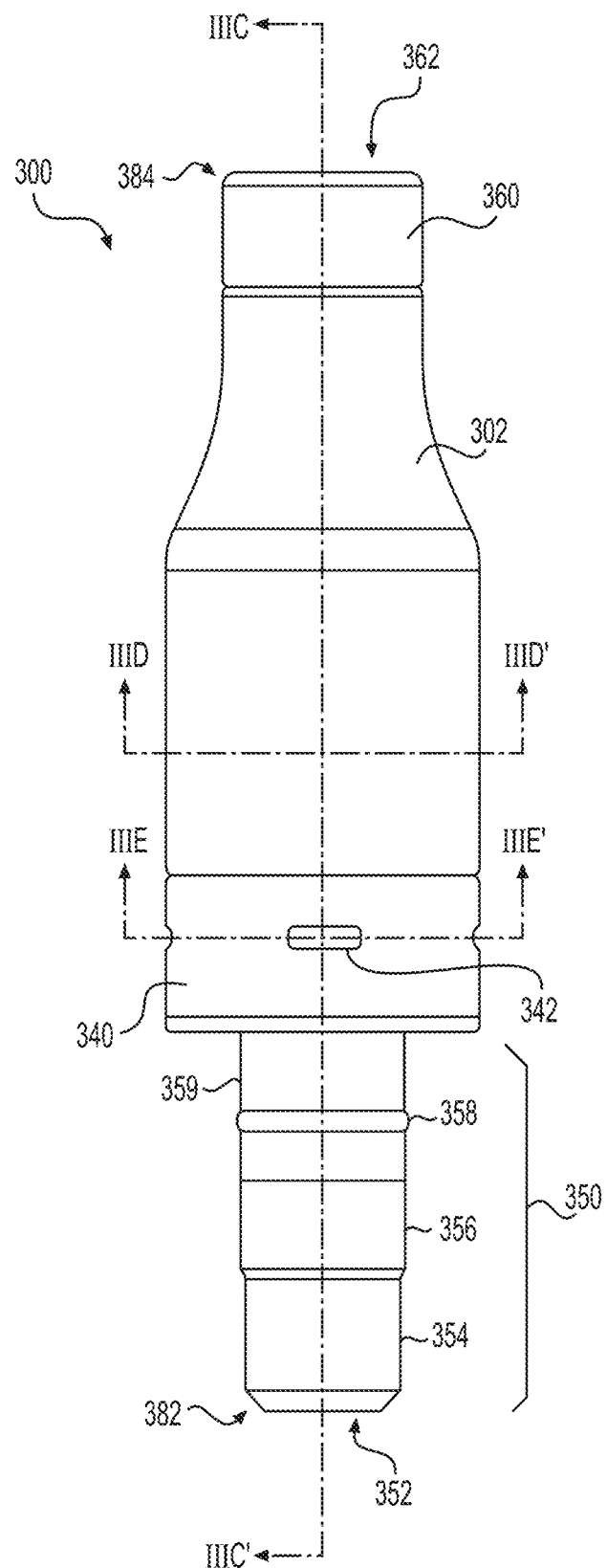
FIG. 3B is a plan side view of the tip device of FIG. 3A.
Figure 3C:
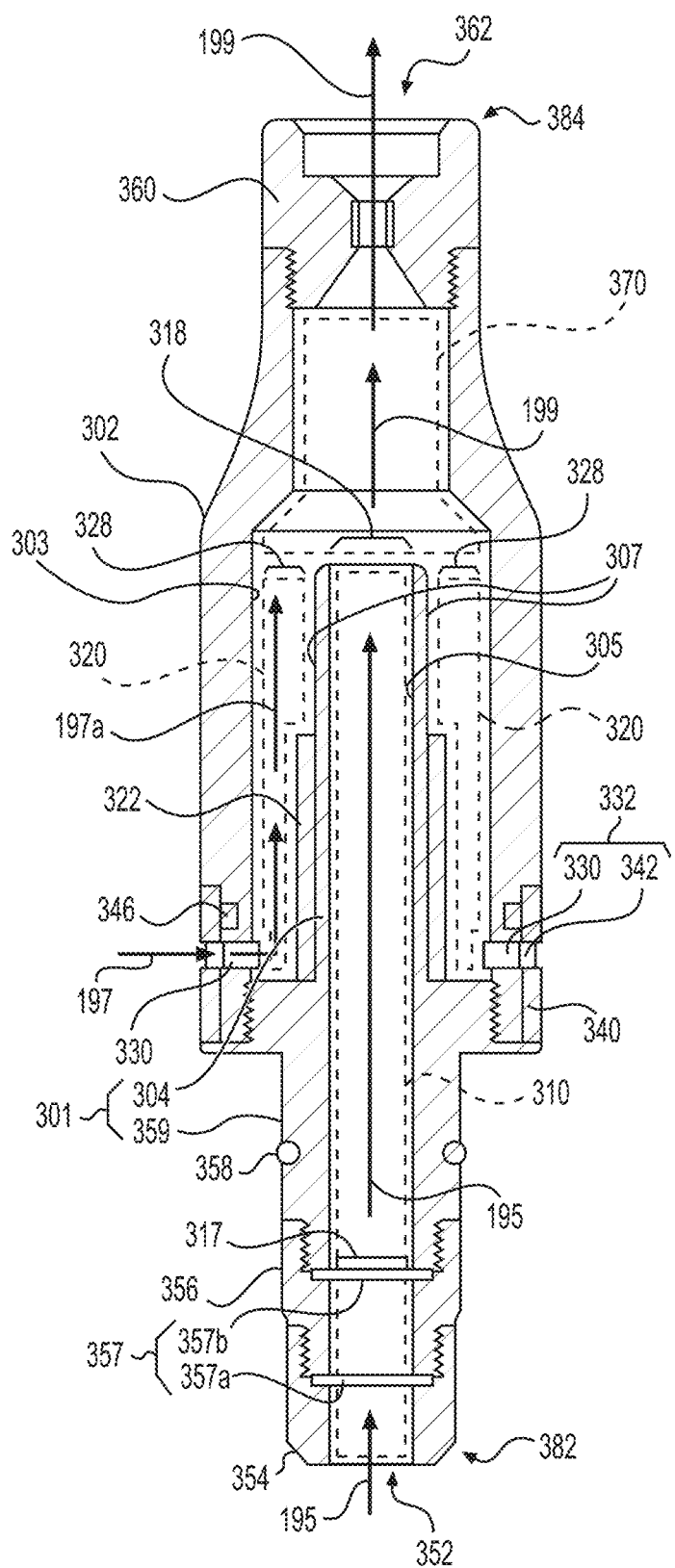
FIG. 3C is a plan cross-sectional view of the tip device of FIG. 3B along cross-sectional view line IIIC-IIIC', according to some example embodiments.
Figure 3D:
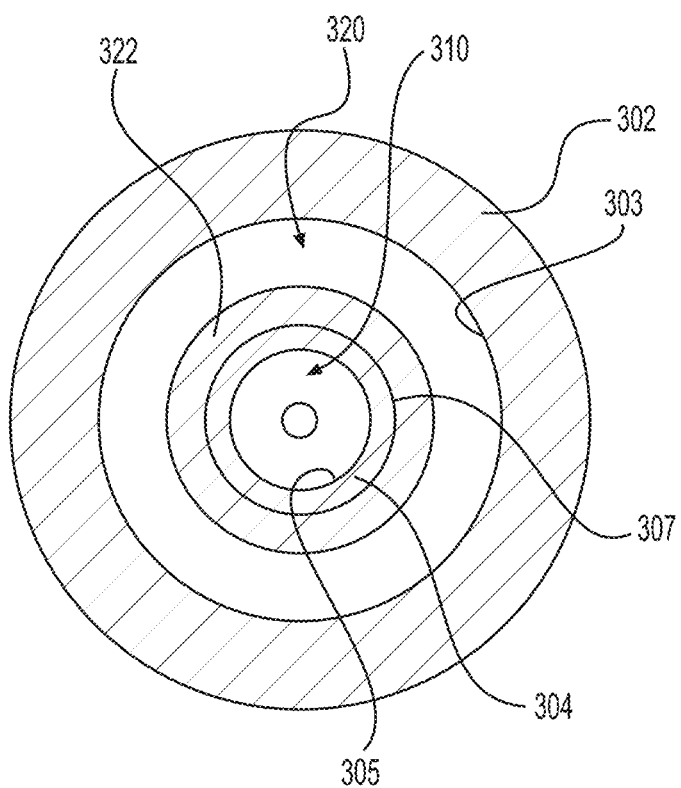
FIG. 3D is a plan cross-sectional view of the tip device of FIG. 3B along cross-sectional view line IIID-IIID', according to some example embodiments.
Figure 3E:
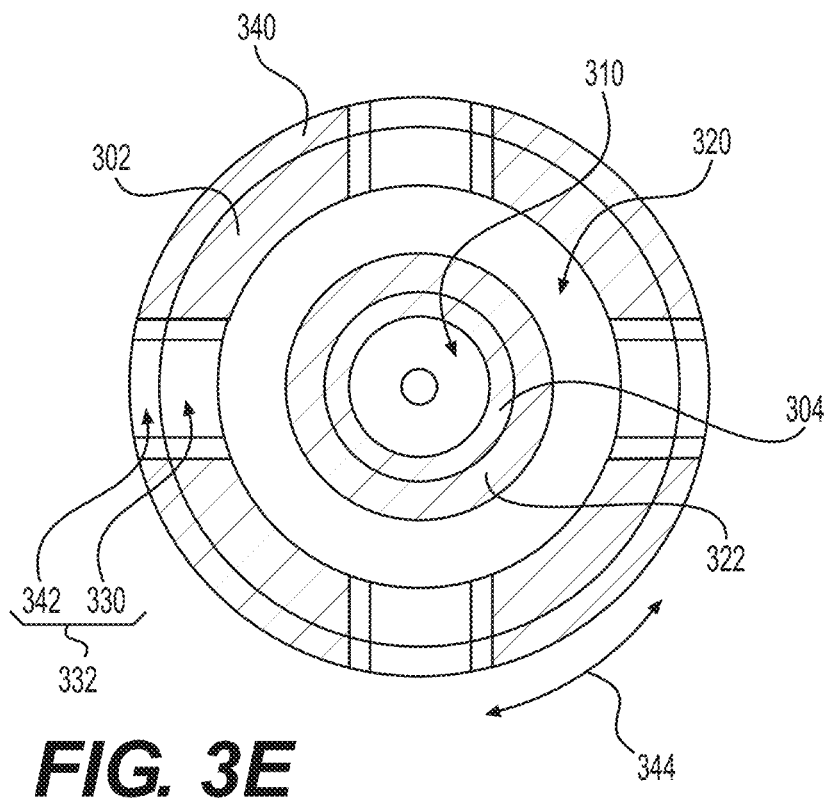
FIG. 3E is a plan cross-sectional view of the tip device of FIG. 3B along cross-sectional view line IIIE-IIIE', according to some example embodiments.

FIG. 3A is a perspective view of a tip device 300 according to some example embodiments. FIG. 3B is a plan side view of the tip device 300 of FIG. 3A. FIG. 3C is a plan cross-sectional view of the tip device 300 of FIG. 3B along cross-sectional view line IIIC-IIIC', according to some example embodiments. FIG. 3D is a plan cross-sectional view of the tip device 300 of FIG. 3B along cross-sectional view line IIID-IIID', according to some example embodiments. FIG. 3E is a plan cross-sectional view of the tip device 300 of FIG. 3B along cross-sectional view line IIIE-IIIE', according to some example embodiments.

Each of the example embodiments of the tip device 300 shown in FIGS. 3A-3E may be included in any of the embodiments included herein, including the tip device 160 shown in FIGS. 1A-2C. In some example embodiments, any of the elements of the tip device 300 shown in FIGS. 3A-3E may be included in the tip device 160 shown in FIGS. 1A-2C. In some example embodiments, the tip device 160 shown in FIGS. 1A-2C may be the same or substantially the same (e.g., the same within manufacturing tolerances and/or material tolerances) as the tip device 300 shown in FIGS. 3A-3E.

In some example embodiments, the tip device 300 is configured to receive and direct a generated vapor 195 through a first conduit 310 of the tip device 300, receive and direct a separate air flow 197 through a separate, second conduit 320 of the tip device 300, mix the generated vapor 195 and the air flow 197 to form a mixed vapor 199, and direct the mixed vapor 199 out of the tip device 300. The tip device may be configured to physically isolate the second conduit 320 from the first conduit 310 via an instance of interposing structure, and the tip device 300 may further include an additive material 322 on a surface that at least partially defines the second conduit 320, so that an additive may be released into the air flow 197 directed (e.g., "drawn") through the second conduit 320 independently of any fluid (e.g., generated vapor 195) passing through the first conduit 310 of the tip device 300. The air flow 197 and the generated vapor may be mixed after the respective air flow 197 and generated vapor 195 have been directed out of the respective outlet ends 328 and 318 of the second conduit 320 and the first conduit 310, so that mixing of the air flow 197 and the generated vapor 195 to form a mixed vapor 199 occurs "downstream" of the first and second conduits 310 and 320.

As a result of the above-mentioned structural configuration of the tip device 300 in relation to the first and second conduits 310 and 320 and the physical isolation thereof, the additive material 322 in the second conduit 320 may be physically isolated from the first conduit 310, thereby reducing or minimizing the probability of interaction between the additive held in the additive material 322 and a pre-vapor formulation that may be held in an external source (e.g., cartridge 110) coupled to the tip device 300 in fluid communication with the first conduit 310 of the tip device 300. Based on reducing and/or minimizing the probability of such interactions, the reliability and/or consistency of the mixed vapor 199 generated based on mixing of the air flow 197 and the generated vapor 195 may be improved, thereby improving the sensory experience provided by an e-vaping device that includes the tip device 300 based on improving the reliability and/or consistency of the experience provided by the mixed vapor 199.

In addition, based on physically isolating the additive material 322 in the tip device 300, relative to at least the pre-vapor formulation held in an external source (e.g., cartridge 110), the ability to customize the properties of a mixed vapor 199 provided by an e-vaping device that includes the tip device 300 may be improved, as one or more portions of the tip device 300 that include an additive material 322 may be swapped or replaced (or different tip devices 300 having different additive materials with different additives may be swapped or replaced from being coupled to the external source), thereby enabling the customization of properties of a mixed vapor 199 provided via mixing of a generated vapor 195 with different additives in the tip device 300. As a result, the sensory experience that may be provided by an e-vaping device that includes the tip device 300 may be improved as a result of enabling customization of the sensory experience via enabling swapping and/or replacing of one or more additives held in the tip device 300, independently of changing pre-vapor formulation held in an external source (e.g., cartridge 110) that is used to generate the generated vapor 195.

Referring to FIGS. 3A-3E, the tip device 300 includes an outer housing structure 302, a conduit structure 301, an inlet structure 354, an additional additive assembly 356, and an outlet assembly 360. The aforementioned structures are configured to be coupled together to establish the tip device 300 and the various elements, conduits, and spaces included therein.

First Conduit and Second Conduit with Physically Isolated Additive Material

Referring to FIGS. 3A-3E, in some example embodiments, a tip device 300 includes a first conduit structure having a surface at least partially defining a first conduit having an inlet end and an opposite outlet end, the first conduit structure configured to receive a generated vapor from an external source via the inlet end of the first conduit and direct the received generated vapor through the first conduit towards the outlet end of the first conduit.

For example, as shown in FIGS. 3A-3E, the tip device 300 includes a conduit structure 301, including tube structure 304 and base structure 359, having an inner surface 305 that at least partially defines a first conduit 310 having an inlet end and an opposite outlet end 318. In some example embodiments, because the first conduit 310 may be further defined by additional structures 356 and 354 as described further below, the inlet end of the first conduit 310 that is at least partially defined by the inner surface 305 of the conduit structure 301 may be understood to be the inlet 352, in addition or in alternative to inlet end 317 of conduit structure 301.

As further shown in FIGS. 3A-3E, the conduit structure 301 at least partially defines a first conduit 310 that is in fluid communication with the inlet 352 of the tip device 300, such that the conduit structure 301 will be understood to be configured to receive a generated vapor 195 from an external source (e.g., cartridge 110 shown in FIGS. 1A-2C) via the inlet end of the first conduit 310. The conduit structure 301 is further configured to direct the received generated vapor 195 through the first conduit 310 towards the outlet end 318 of the first conduit 310.

Because the conduit structure 301 at least partially defines the first conduit 310, the conduit structure 301 may be understood to be the "first conduit structure," as the term is understood herein.

Still referring to FIGS. 3A-3E, in some example embodiments, a tip device 300 includes a second conduit structure having a surface at least partially defining a second conduit having an inlet end and an opposite outlet end, the second conduit structure configured to receive an air flow from an ambient environment via the inlet end of the second conduit and direct the air flow through the second conduit towards the outlet end of the second conduit.

For example, as shown in FIGS. 3A-3E, the tip device 300 includes an outer housing structure 302 having an inner surface 303 that at least partially defines a second conduit 320 having an inlet end 330 and an opposite outlet end 328. As further shown in FIGS. 3A-3E, the inlet end 330 is in fluid communication with an ambient environment via an air port 342 of an adjustable flow control assembly 340 (described further below), such that the inlet end 330 and air port 342 collectively comprise an inlet 332 of the second conduit 320, where the cross-sectional flow area of the inlet 332 is adjustable based on adjustment of the adjustable flow control assembly 340 (described further below). Restated, the inlet end 330 may be understood to be a conduit extending from the second conduit 320 through the outer housing structure 302 to an outer surface of the outer housing structure 302, and the air port 342 may be understood to be a conduit extending through the structure of the adjustable flow control assembly 340 to the ambient environment, such that the inlet end 330 and the air port 342 may collectively comprise an air inlet 332 that is a conduit extending from the second conduit 320 to the ambient environment, through the structure (e.g., "interior") of both the outer housing structure 302 and the adjustable flow control assembly 340. Thus, the air inlet 332 may be understood to be, in some example embodiments, an adjustable conduit comprising the inlet end 330 and the air port 342 and having an adjustable cross-sectional flow area based on adjustable movement of the air port 342 in relation to the inlet end 330 via movement of the adjustable flow control assembly 340 in relation to the outer housing structure 302. In some example embodiments, the adjustable flow control assembly 340 is omitted from tip device 300, such that the inlet end 330 is the inlet 332 of the second conduit 320.

Based on the inlet end 330 of the second conduit 320, the inlet end 330 being an inlet port that extends through the outer housing structure 302 between an outer surface of the outer housing structure 302 and the inner surface 303, the outer housing structure 302 will be understood to be configured to receive an air flow 197 from an ambient environment via the inlet end 330 of the second conduit 320 and direct the air flow 197 through the second conduit 320 towards the outlet end 328 of the second conduit 320.

As further shown in FIGS. 3A-3E, the conduit structure 301 includes a tube structure 304 that extends coaxially with the inner surface 303 of the outer housing structure 302 along a common longitudinal axis of the first conduit 310. As a result, as shown in FIGS. 3C-3E, while an inner surface 305 of the tube structure 304 of the conduit structure 301 at least partially defines an outer boundary of the first conduit 310, an outer surface 307 of the same tube structure 304 at least partially defines an inner boundary of the second conduit 320, with the inner surface 303 of the outer housing structure 302 at least partially defining an outer boundary of the second conduit 320. As a result, and as shown in FIGS. 3C-3E, the second conduit 320 is defined to be an annular conduit that surrounds the first conduit and extends coaxially with the first conduit along the longitudinal axis of the first conduit 310, while the first and second conduits 310 and 320 are physically isolated from each other between the respective inlet ends and outlet ends of the first and second conduits 310 and 320 by at least the tube structure 304 of the conduit structure 301.

As a result, because a surface of the tube structure 304 at least partially defines the second conduit 320, at least the tube structure 304 of the conduit structure 301 may be understood to be a "second conduit structure" of the tip device 300, in addition to being understood to be a "first conduit structure" of the tip device 300. Restated, a structure within the tip device 300 may be understood to be one or both of a first conduit structure and a second conduit structure. A structure that at least partially defines both the first conduit and the second conduit, e.g., the tube structure 304, may be understood herein to be an "interposing structure" of the tip device 300. Such an interposing structure may, as shown with respect to at least the tube structure 304 in FIGS. 3C-3E, be a structure that physically isolates the first and second conduits 310 and 320 from each other.

In the example embodiments shown in FIGS. 3A-3E, where the tube structure 304 is understood to be an "interposing structure" as described further below, such an interposing structure includes a hollow cylindrical structure having an inner surface 305 and an outer surface 307 extending along a longitudinal axis, such that the first conduit 310 is a cylindrical conduit and the second conduit 320 is an annular conduit surrounding the first conduit 310 and extending coaxially with the first conduit 310 along the same longitudinal axis ("a common longitudinal axis"), the second conduit 320 at least partially defined by at least the outer surface 307 of the interposing structure (tube structure 304).

In some example embodiments, including the example embodiments shown in FIGS. 3C-3E with regard to the "interposing structure" that is the tube structure 304, a tip device 300 may include an interposing structure that is common to both the first conduit structure and the second conduit structure, such that the interposing structure at least partially defines both the first conduit 310 and the second conduit 320. Furthermore, in some example embodiments, the interposing structure includes opposite surfaces at least partially defining separate conduits of the first conduit and the second conduit. For example, as shown in FIGS. 3C-3E, where the tube structure 304 is an interposing structure of the tip device 300, the inner surface 305 of the tube structure 304 that at least partially defines the first conduit 310 and the outer surface 307 of the tube structure 304 that at least partially defines the second conduit 320 are opposite surfaces at least partially defining separate conduits of the first conduit 310 and the second conduit 320.

In some example embodiments, where the tip device 300 includes an interposing structure, the interposing structure may include a hollow cylindrical structure having an inner surface and an outer surface extending along a longitudinal axis, the first conduit may be a cylindrical conduit; and the second conduit may be an annular conduit surrounding the first conduit and extending coaxially with the first conduit along the longitudinal axis, where the second conduit is at least partially defined by at least the outer surface of the interposing structure.

For example, as shown in FIGS. 3C-3E, the tube structure 304 that is an "interposing structure" is a hollow cylindrical structure having an inner surface 305 and an outer surface 307 extending along a longitudinal axis of the first conduit 310, such that the first conduit 310 is a cylindrical conduit and the second conduit 320 is an annular conduit surrounding the first conduit 310 and extending coaxially with the first conduit along the longitudinal axis of the first conduit, such that the second conduit 320 is at least partially defined by at least the outer surface 307 of the tube structure 304.

Still referring to FIGS. 3C-3E, in some example embodiments a second conduit structure of the tip device 300 includes an additive material on a surface of the second conduit structure. The additive material may include an additive, and the flavor material may be configured to release the additive into the air flow 197 directed through the second conduit 320, such that the additive mixes with the air flow 197 to form a mixed air flow 197a that is directed through the outlet end 328 of the second conduit 320. In some example embodiments, the "mixed air flow 197a" may be referred to herein as simply an "air flow" into which additive has been released.

For example, as shown in FIGS. 3C-3E, the tip device 300 includes an additive material 322 on the outer surface 307 of the tube structure 304, such that the additive material 322 is in fluid communication with the second conduit 320 at least partially defined by the outer surface 307 of the tube structure 304. An air flow 197 drawn into the second conduit 320 via the inlet end 330 of the second conduit 320 may thus be directed to flow through the second conduit 320 in fluid communication with the additive material 322 such that the additive material 322 releases one or more additive materials into the air flow 197 to form the mixed air flow 197. The mixed air flow 197, thus including the released additive, may be directed through the outlet end 328 of the second conduit 320 to be mixed with the generated vapor 195 in a downstream conduit in the tip device 300.

While FIGS. 3C-3E illustrate an additive material 322 on the outer surface 307 of the tube structure 304 (the tube structure 304 understood in FIGS. 3C-3E to be a second conduit structure by virtue of at least partially defining the second conduit 320), in some example embodiments an additive material may be on the inner surface 303 of the outer housing structure 302, in addition or in alternative to the additive material 322.

In some example embodiments, the additive material 322 may at least partially extend transverse to a longitudinal axis of the second conduit 320, so that the second conduit 320 is configured to direct the air flow 197 to pass at least partially through an interior of the additive material 322 in order for the air flow 197 to be directed toward the outlet end 328 of the second conduit 320.

The additive material 322, as described herein, may include a porous structure. The porous structure may hold an additive in fluid communication with the second conduit 320, so that the air flow 197 may pass at least partially through the porous structure and in fluid communication with the additive held in the porous structure. The air flow 197 may act as an eluent, eluting the additive from the porous structure and into the air flow 197 to form an eluate. The eluate may include a mixture of air flow 197 and the additive. Such an eluate may be referred to as the mixed air flow 197a.

In some example embodiments, an additive eluted into the air flow 197 is in a particulate phase. A particulate phase may include a liquid phase, solid phase, or the like. In some example embodiments, an additive eluted into the air flow 197 is in a vapor phase, gas phase, etc. An additive may include a volatile flavor substance, and the volatile flavor substance may be eluted into the air flow 197. In some example embodiments, an additive eluted into the air flow 197 includes a nonvolatile flavor substance.

Still referring to FIGS. 3C-3E, in some example embodiments, the tip device 300 includes at least an interposing structure of the first conduit structure and the second conduit structure that physically isolates the additive material of the tip device 300 from the first conduit, such that the additive material is configured to release the additive into the air flow directed through the second conduit 320 independently of the generated vapor 195 directed through the first conduit 310.

For example, as shown in FIGS. 3C-3E, the tube structure 304, being an interposing structure as described above, physically isolates the additive material 322 from the first conduit 310 at least partially defined by the inner surface 305, such that the additive material 322 is configured to release additive into an air flow 197 directed through the second conduit 320 independently of a fluid (e.g., a generated vapor 195) that is directed through the first conduit 310. If and/or when an additive material is on the inner surface 303 of the outer housing structure 302, the tube structure 304 is still configured to physically isolate such an additive material from the first conduit 310 at least partially defined by the inner surface 305 of the tube structure 304.

In some example embodiments, if and/or when the additive material 322 that holds the additive is physically isolated from the first conduit 310 that is configured to receive the generated vapor 195 from an external source, and the first and second conduits 310 and 320 respectively direct the generated vapor 195 and the mixed air flow 197a to the respective outlet ends 318 and 328 of the first and second conduits 310 and 320, the generated vapor 195 may be cooled from an initial temperature at formation in the external source if and/or when the generated vapor 195 and the mixed air flow 197a mix in a space and/or conduit that is in fluid communication with both of the outlet ends 318 and 328. Where the generated vapor 195 mixing with the mixed air flow 197a is cooled from the initial temperature, and where the mixed air flow 197a includes an additive released from the additive material 322, chemical reactions between the additive included in the mixed air flow 197a and the elements of the generated vapor 195 may be at least partially mitigated.

In some example embodiments, if and/or when the additive material 322 that holds the additive is physically isolated from the first conduit 310 that is configured to receive the generated vapor 195 from an external source, and the first and second conduits 310 and 320 respectively direct the generated vapor 195 and the mixed air flow 197a to the respective outlet ends 318 and 328 of the first and second conduits 310 and 320, the tip device 300 may be configured to mitigate a probability of chemical reactions between the additive and one or more elements of the external source. An absence of such chemical reactions may result in an absence of reaction products in the mixed vapor 199 that is formed through the mixing of the mixed air flow 197a that holds additives released from the additive material 322 and the generated vapor 195. As a result, a tip device 300 that is configured to mitigate the probability of such chemical reactions may provide a more consistent and improved sensory experience through the mixed vapor 199.

Outlet Assembly

Still referring to FIGS. 3A-3E, in some example embodiments a tip device 300 includes an outlet assembly configured to receive the air flow and the generated vapor from the respective outlet ends of the first and second conduits, mix the air flow and the generated vapor to establish a mixed vapor, and direct the mixed vapor out of the tip device.

For example, as shown in at least FIG. 3C, the tip device 300 includes an outlet assembly 360 that defines an outlet 362 of the tip device 300 at an outlet end 384 of the tip device 300. The outlet assembly 360 is illustrated to be coupled to the outer housing structure 302, but it will be understood that the outlet assembly 360 may be coupled to one or more other structures of the tip device 300. For example, in some example embodiments, the outlet assembly 360 may be integrated with the outer housing structure 302, such that the outlet assembly 360 and outer housing structure 302 comprise a continuous instance of material that is coupled to the conduit structure 301.

As shown in FIG. 3C, the outlet assembly 360 at least partially defines a mixing conduit 370 within the tip device 300, where the mixing conduit 370 is further defined by an inner surface of the outer housing structure 302 and the outlet ends 318 and 328 of the first and second conduits 310 and 320. Because both outlet ends 318 and 328 at least partially define the mixing conduit 370, the first and second conduit structures (e.g., conduit structure 301 and outer housing structure 302) are configured to direct the generated vapor 195 and the mixed air flow 197a into the common mixing conduit 370 via the respective outlet ends 318 and 328. Upon reaching the mixing conduit 370, the mixed air flow 197a may mix with the generated vapor 195 to form a mixed vapor 199. As shown in FIG. 3C, the outlet assembly 360 defines the outlet 362 of the tip device 300, where the outlet 362 is in fluid communication with the mixing conduit 370 such that the outlet assembly 360 is configured to direct the mixed vapor 199 out of the tip device 300, from the mixing conduit 370, via the outlet 362.

In some example embodiments, the mixing conduit 370 is absent from the tip device 300. For example, the outlet assembly 360 may be directly coupled to each of the outlet ends 318 and 328 of the first and second conduits 310 and 320, wherein one or more inner surfaces of the outlet assembly 360 define an internal mixing conduit and wherein the mixed air flow 197a and generated vapor 195, received into the outlet assembly 360 interior via respective outlet ends 328 and 318, may be directed by the interior structure of the outlet assembly 360 to be mixed within the interior of the outlet assembly 360 to form the mixed vapor 199 and to be directed out of the outlet assembly 360 via outlet 362.

Adjustable Flow Control Assembly

Still referring to FIGS. 3A-3E, in some example embodiments, a tip device 300 includes an adjustable flow control assembly coupled to the inlet end of the second conduit, the adjustable flow control assembly configured to adjustably control an effective cross-sectional flow area of the inlet end to control a flow rate of air drawn into the second conduit via the inlet end of the second conduit.

For example, as shown in FIGS. 3A-3E, the tip device 300 may include an adjustable flow control assembly 340 that extends around an outer circumference of the outer housing structure 302 and is configured to be adjustably rotated ("spun") 344 around the circumference of the outer housing structure 302. As shown, the adjustable flow control assembly 340 includes a plurality of air ports 342 that are configured to be at least partially aligned with one or more inlet ends 330 of the second conduit 320 based on the rotation of the adjustable flow control assembly 340 around the circumference of the outer housing structure 302.

Based on the adjustable flow control assembly 340 being adjustably rotated, the alignment of one or more air ports 342 with one or more inlet ends 330 may be adjustably controlled. Collectively, an air port 342 and an inlet end 330 may form an air inlet 332 of the second conduit 320. When fully aligned with an inlet end 330, an air port 342 may enable a maximum effective cross-sectional flow area of the inlet end 330 to be exposed to the ambient environment, thereby establishing a maximum cross-sectional flow area of the air inlet 332.

Based on the adjustable flow control assembly 340 being rotated to progressively move the air port 342 in or out of alignment with the inlet end 330, the effective cross-sectional flow area of the inlet end 330, and thus the cross-sectional flow area of the air inlet 332, may be adjustably controlled.

Based on adjustable enabling control of the cross-sectional flow area of the air inlet 332, and because the maximum flow rate of the air flow 197 that may be drawn into the second conduit 320 may be associated with the cross-sectional flow area of the air inlet 332, the flow rate of the air flow 197 through the second conduit 320 may be controlled independently of a flow rate of the generated vapor 195 through the first conduit 310. Because the flow rate of the air flow 197 may be controlled independently of the flow rate of the generated vapor 195, the amount of mixed air flow 197a that is mixed with the generated vapor 195, and thus the amount of additive that is mixed with the generated vapor 195 to form the mixed vapor 199 may be controlled based on adjustably controlling a position of the adjustable flow control assembly 340. Thus, the adjustable flow control assembly 340 provides improved control over the sensory experience provided by the tip device 300 via control over the amount of additive included in the mixed vapor 199.

As shown in FIG. 3C, the adjustable flow control assembly 340 may be located in a notched "track" extending around the outer surface of the outer housing structure 302, where the adjustable flow control assembly 340 further includes one or more bearings 346 configured to enable smooth adjustable movement of the adjustable flow control assembly 340. However, in some example embodiments one or both of the track and the bearings 346 may be omitted.

Inlet Interface

As illustrated, the tip device 300 includes an inlet interface 350 that includes an inlet 352 of the tip device 300 at an inlet end 382 of the tip device 300. The inlet interface 350 is configured to couple with an external source (e.g., a cartridge including the cartridge 110 illustrated in FIGS. 1A-2C) that is configured to provide a generated vapor 195. In some example embodiments, the tip device 300 is configured to be reversibly coupled to an external source (e.g., cartridge 110) via reversible coupling of inlet interface 350 with an outlet interface (e.g., outlet interface 118) of the external source. The inlet interface 350 is configured to be inserted into an outlet interface of the external source (e.g., outlet interface 118) to establish an airtight or substantially airtight seal between the inlet interface 350 and the outlet interface of the external source. As a result, the inlet interface 350 is configured to be coupled with an outlet interface of the external source such that an entirety or substantially an entirety (e.g., an entirety within manufacturing tolerances and/or material tolerances) of the generated vapor 195 provided from the external source via the outlet interface of the external source is received into the tip device 300 via the inlet 352 included in the inlet interface 350.

In some example embodiments, the inlet interface 350 includes at least one structure of the base structure 359 of the conduit structure 301, the additional additive assembly 356, and inlet structure 354 that are coupled together via complementary interfaces to establish the inlet interface. In some example embodiments, one or more structures of the additional additive assembly 356 and the inlet structure 354 may be omitted from the tip device 300. For example, additional additive assembly 356 may be omitted and the base structure 359 may be directly coupled to the inlet structure 354. In another example, inlet structure 354 may be omitted and the additional additive assembly 356 may define the inlet 352. In another example, additional additive assembly 356 and inlet structure 354 may be omitted, and the base structure 359 may define the inlet 352.

In some example embodiments, the inlet interface 350 may include one or more sealing elements configured to at least partially establish an airtight or substantially airtight seal between the inlet interface 350 and an external source to which the tip device 300 is coupled if and/or when the inlet interface 350 is inserted into an outlet interface of the external source. As shown in FIGS. 3A-3E, the one or more sealing elements may include one or more ring-shaped gaskets 358 that may be included within one or more respective notch structures on an outer surface of one or more structures of the inlet interface 350. The illustrated tip device 300 includes an individual ring-shaped gasket 358 in a notch on an outer surface of the base structure 359, but it will be understood that additional sealing elements may be included on an outer surface of one or more structures of the base structure 359, the additional additive assembly 356, and the inlet structure 354. In some example embodiments, the notch illustrated in FIG. 3C may be absent, and the sealing element may be coupled (e.g., held in place by friction, adhered to by one or more adhesives, welded, etc.) to an outer surface of one or more structures of the inlet interface 350.

Additional Additive Assembly

Still referring to the inlet interface 350 of the tip device, in some example embodiments, a tip device 300 may include an additional additive assembly 356 in fluid communication with the first conduit 310, the additional additive assembly 356 configured to release an additional additive into the generated vapor 195 that is directed through the first conduit 310, such that the generated vapor 195 directed through the outlet end 318 of the first conduit 310 includes the additional additive released by the additional additive assembly 356, separately from the additive released by the additive material into the air flow 197 in the second conduit 320.

At shown in FIG. 3C, the tip device 300 may include an additional additive assembly 356 that includes an inner surface at least partially defining a portion of the first conduit 310 and further including one or more additional additive structures 357, including for example additive structures 357a and 357b as shown in FIG. 3C, configured to release an additional additive into a fluid (e.g., the generated vapor 195) that is directed through the first conduit 310 towards the outlet end 318 of the first conduit 310.

As shown in FIG. 3C, where the additional additive assembly 356 is coupled to an inlet end 317 of the conduit structure 301, the additional additive assembly 356 may include additive structures 357a and 357b that extend transversely across the respective inlet ends and outlet ends of the additional additive assembly 356. One of the additive structures 357a and 357b may be omitted, such that the additional additive assembly 356 includes an individual additive structure that extends transversely across the inlet end or outlet end of the portion of the first conduit 310 defined by an inner surface of the additional additive assembly 356. In some example embodiments, the additional additive assembly 356 includes, in addition or in alternative to the transversely-extending additive structures 357a and 357b, an additive structure that extends along an inner surface of the additional additive assembly 356 that defines a portion of the first conduit 310 when the additional additive assembly 356 is coupled to the base structure 359; such an additive structure may extend at least partially coaxially with a longitudinal axis of the portion of the first conduit 310 that is at least partially defined by the inner surface of the additional additive assembly 356.

The one or more additive structures 357 of the additional additive assembly 356 may include one or more additives, referred to herein as "additional additives," that may be released into a fluid (e.g., the generated vapor 195) that is directed (e.g., "drawn") through the first conduit 310. Such one or more additional additives may include one or more flavorants. The one or more additional additives may include one or more additives that are known to exhibit reduced and/or minimal interactions with pre-vapor formulation that may be held in an external source (e.g., cartridge 110) that may be coupled to the inlet interface 350 of the tip device 300, in relation to the one or more additives that may be held in the additive material 322.

In some example embodiments, an additive structure 357 included in the additional additive assembly 356 (e.g., one or more of the additive structures 357a and 357b) may be a porous structure, mesh structure, matrix structure, some combination thereof, or the like, wherein the additive structure is configured to direct a fluid passing through the first conduit 310 to pass through an interior of the additive structure such that one or more additives are released from the additive structure into the fluid that is passing through the interior of the additional additive assembly 356.

Furthermore, it will be understood that the additional additive assembly 356 may be reversibly ("removably") coupled to the base structure 359, such that the additional additive assembly 356 may be swapped for another additional additive assembly 356 that may include a different one or more additive structures 357 holding a different one or more additional additives. As a result, the additional additive assembly 356 enables improved customization of the sensory experience provided by the tip device 300.

Figure 4A:
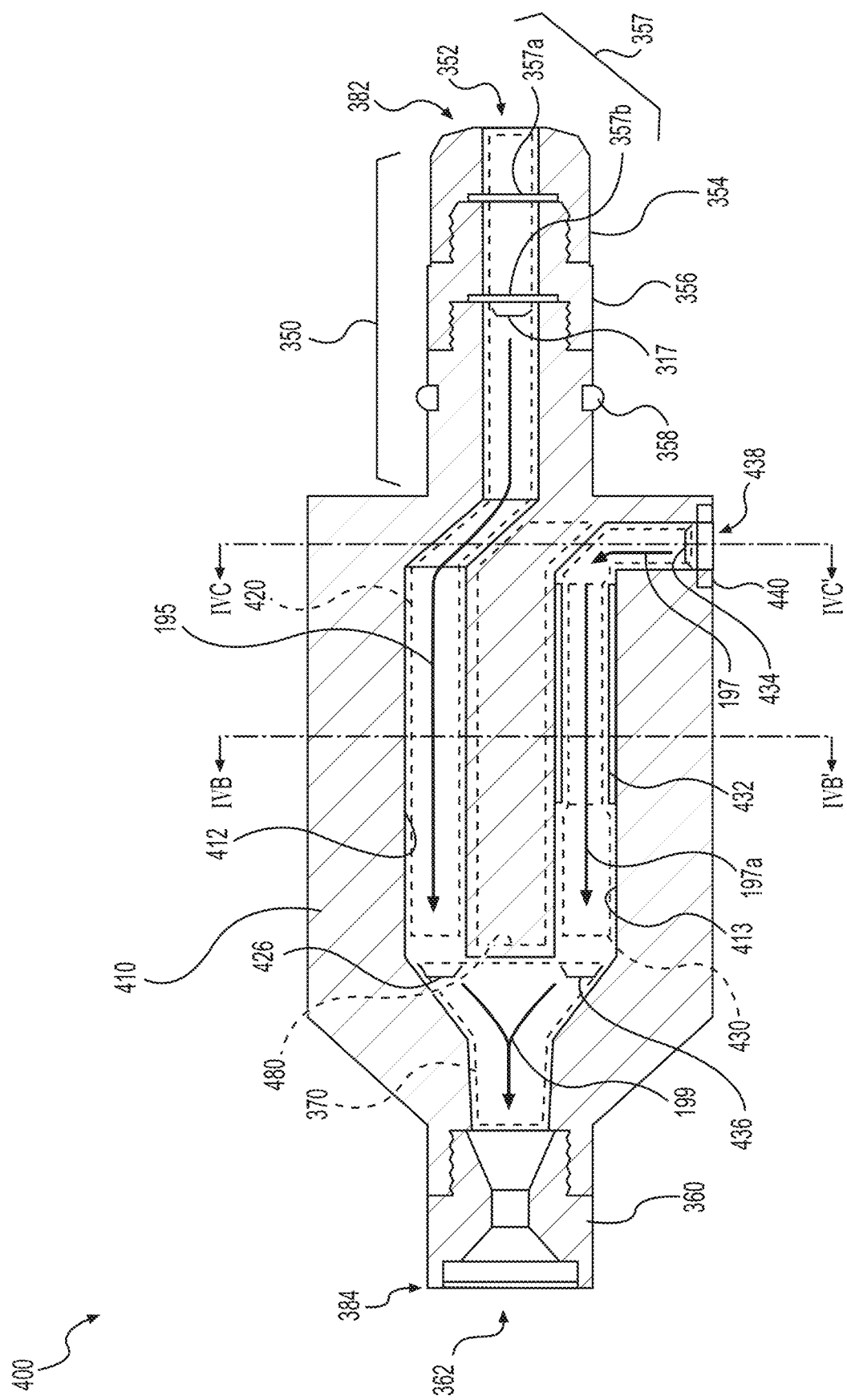
FIG. 4A is a plan side cross-sectional view of a tip device according to some example embodiments.
Figure 4B:
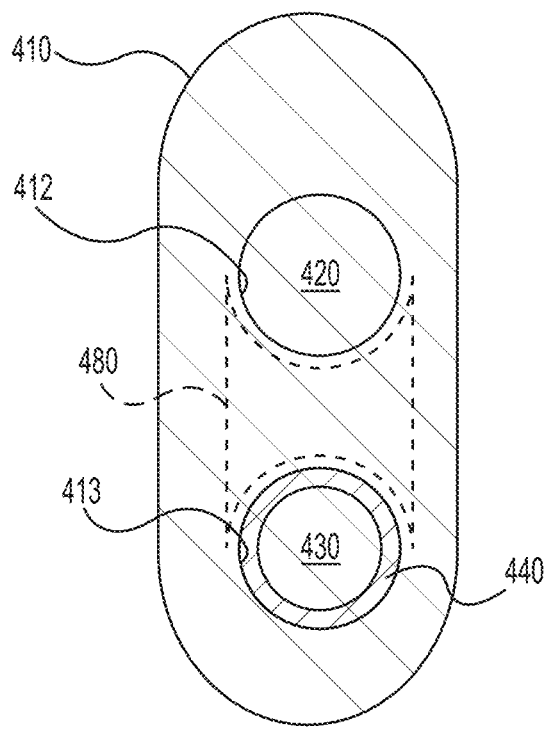
FIG. 4B is a cross-sectional view of the tip device of FIG. 4A along cross-sectional view line IVB-IVB', according to some example embodiments.
Figure 4C:
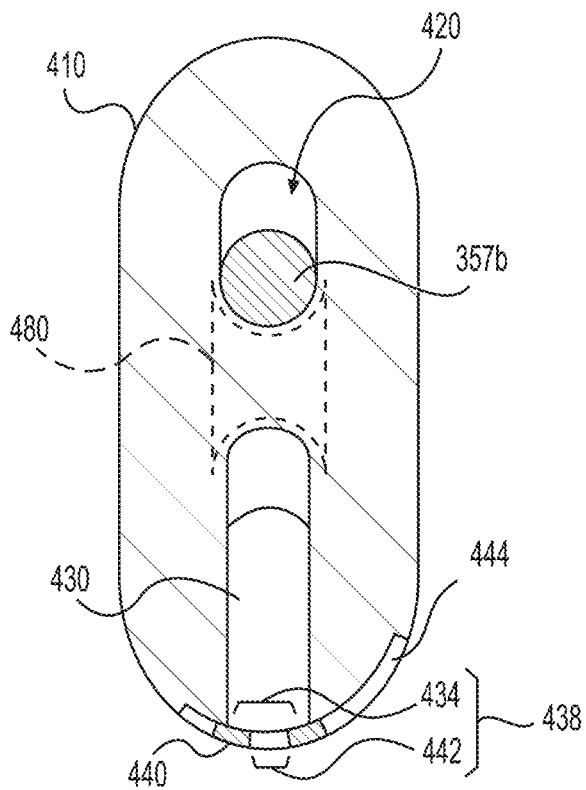
FIG. 4C is a cross-sectional view of the tip device of FIG. 4A along cross-sectional view line IVC-IVC', according to some example embodiments.

FIG. 4A is a plan side cross-sectional view of a tip device 400 according to some example embodiments. FIG. 4B is a cross-sectional view of the tip device of FIG. 4A along cross-sectional view line IVB-IVB', according to some example embodiments. FIG. 4C is a cross-sectional view of the tip device of FIG. 4A along cross-sectional view line IVC-IVC', according to some example embodiments.

Each of the example embodiments of the tip device 400 shown in FIGS. 4A-4C may be included in any of the embodiments included herein, including the tip device 160 shown in FIGS. 1A-2C. In some example embodiments, any of the elements of the tip device 400 shown in FIGS. 4A-4C may be included in the tip device 160 shown in FIGS. 1A-2C. In some example embodiments, the tip device 160 shown in FIGS. 1A-2C may be the same or substantially the same (e.g., the same within manufacturing tolerances and/or material tolerances) as the tip device 400 shown in FIGS. 4A-4C.

Tip device 400 includes some elements that are the same or substantially the same (e.g., the same within manufacturing tolerances and/or material tolerances) in form and/or function to elements of the tip device 300 illustrated and described with reference to FIGS. 3A-3E. Such elements have common reference labels as elements shown in FIGS. 3A-3E and are not described further with reference to FIGS. 4A-4C.

In some example embodiments, a tip device includes one or more conduit structures that at least partially define at least two, separate conduits that extend along different longitudinal axes. Such different longitudinal axes may be parallel axes. The separate conduits may each have a cylindrical shape, and the respective outlets of the separate conduits may be in fluid communication with a common outlet assembly. The one or more conduit structures may include an individual structure. At least a portion of the individual structure may be an interposing structure that physically isolates the separate conduits, and one conduit of the separate conduits may include an additive material that is thus physically isolated from another conduit of the separate conduits.

For example, in the example embodiments shown in FIGS. 4A-4C, a tip device 400 may include an individual conduit structure 410 that at least partially defines separate conduits 420 and 430 that extend along separate longitudinal axes. In the example embodiments shown in FIGS. 4A-4C, the separate longitudinal axes are parallel, but the example embodiments are not limited thereto.

As shown, conduit structure 410 may at least partially define, via inner surface 412, a first conduit 420 having inlet end (e.g., inlet end 317 and/or inlet 352) and an opposite outlet end 426. The conduit structure 410 is configured to receive a generated vapor 195 from an external source to which the inlet 452 of the tip device 400 may be coupled (e.g., a cartridge 110).

Conduit structure 410 may at least partially define, via inner surface 413, a second conduit 430 having inlet end 434 and an opposite outlet end 436. Inlet end 434 is in fluid communication with air inlet 438 (and may be common with the air inlet 438) and thus the conduit structure 410 may be configured to direct air flow 197 through the second conduit 430 from the air inlet 438 through the second conduit 430 towards outlet end 436. As shown, the tip device 400 may include an additive material 432 on inner surface 413. As shown, conduit structure 410 includes an interposing structure 480 that physically isolates the additive material 432 from the first conduit 420.

As further shown, conduit structure 410 at least partially defines a mixing conduit 370 that is in fluid communication with both outlet ends 426 and 436, such that the conduit structure 410 defines a mixing conduit 370 that is configured to receive both generated vapor 195 from the first conduit 420 via outlet end 426 and mixed air flow 197a from the second conduit 430 via outlet end 436 and is further configured to mix the generated vapor 195 and the mixed air flow 197a to form a mixed vapor 199.

As further shown in FIGS. 4A-4C, a portion of the conduit structure 410, referred to herein as the interposing structure 480, is between the conduits 420 and 430 and thus is an "interposing structure" as described above with reference to FIGS. 3A-3E.

As further shown in FIGS. 4A-4C, the tip device 400 includes an adjustable flow control assembly 440 configured to be moved along a track 444 in the outer surface of the conduit structure 410. The adjustable flow control assembly 440 includes an air port 442 that is similar to the air port 342 illustrated and described above with reference to FIGS. 3A-3E, such that the adjustable flow control assembly 440 is configured to enable adjustable control of the flow of air flow 197 through the second conduit 430 independently of the flow rate of generated vapor 195 through the first conduit 420, and thus enable independent adjustable control of the amount of additive included in the mixed vapor 199, similarly to the adjustable flow control assembly 340 illustrated and described above with reference to FIGS. 3A-3E.

Figure 5:
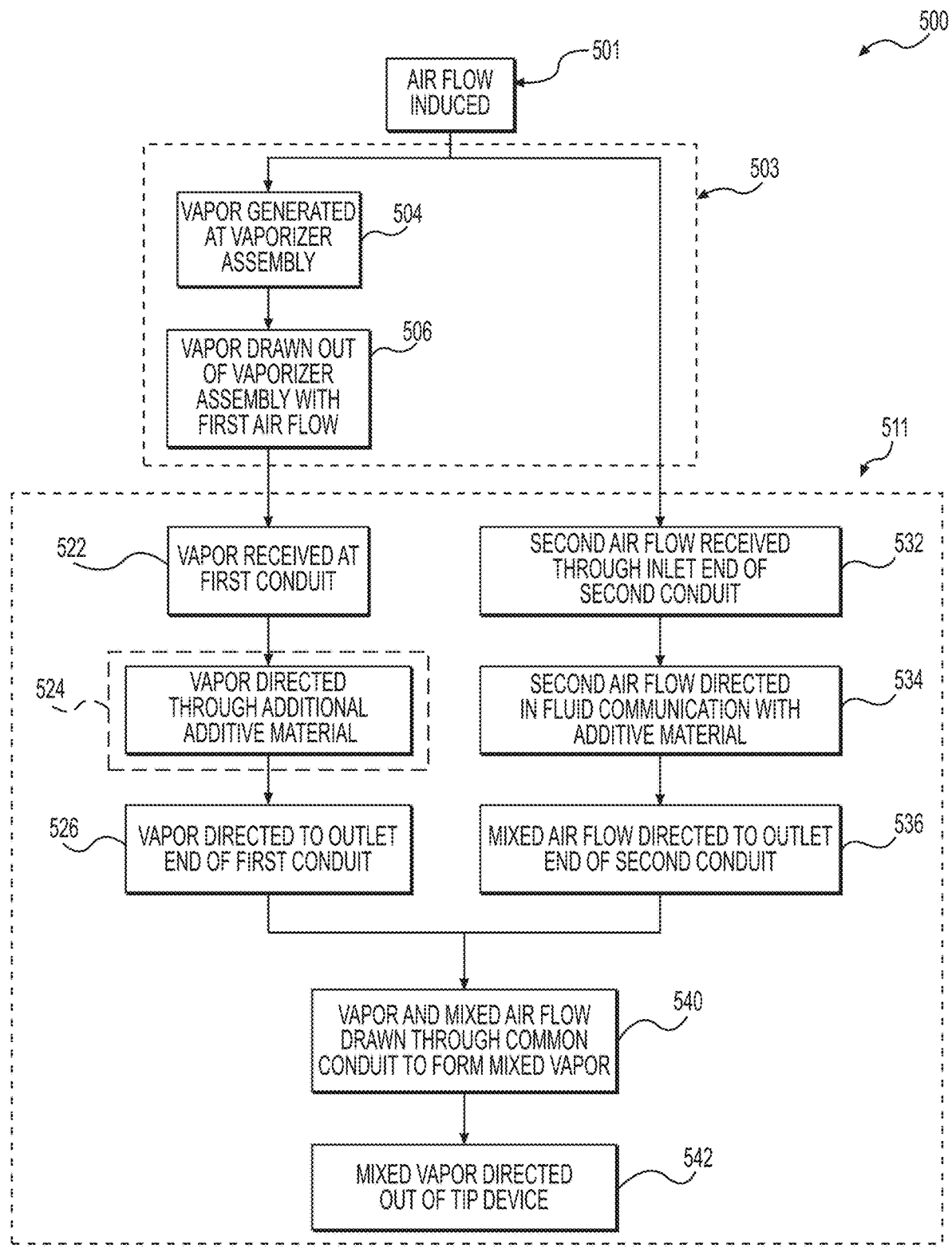
FIG. 5 is an operational flowchart illustrating a method of operation of a tip device according to some example embodiments.

FIG. 5 is an operational flowchart illustrating a method S500 of operation of a tip device according to some example embodiments. The method of operation may be performed with regards to any example embodiment of a tip device as described herein, including the tip device 160 shown in FIGS. 1A-2C, tip device 300 shown in FIGS. 3A-3E, and tip device 400 shown in FIGS. 4A-4C.

At operation S501, an air flow through one or more portions of a tip device may be induced, based on a fluid (e.g., air) being drawn into the tip device via one or more inlets and further drawn through the interior of the tip device towards an outlet of the tip device. The induced air flow may include a first air flow that is induced through an external source (e.g., cartridge 110) and then subsequently through a first conduit of the tip device, and a second air flow that is induced through a second conduit of the tip device.

A set of operations S503, including operations S504-S506, may be performed at an external source (e.g., cartridge 110) that is coupled to an inlet of a tip device. Operations S504-S506 may be performed based on the aforementioned first air flow being induced through the external source and further through a first conduit of the tip device.

At operation S504, a vapor may be generated at a vaporizer assembly of the external source. Such a vapor may be referred to herein as a "generated vapor" (e.g., the generated vapor 195 as described herein).

At operation S506, the generated vapor may be drawn out of the vaporizer assembly, and thus the external source, with the first air flow, such that the generated vapor is drawn into the first conduit of the tip device via an inlet end of the first conduit.

A set of operations S511, including operations S522-S542, may be performed at a tip device as described herein.

Operations S522-S526 are performed with regard to a first conduit of the tip device, as described herein. At operation S522, the aforementioned generated vapor is received at the first conduit of the tip device, with the first air flow, via an inlet end of the first conduit, from the external source from which the generated vapor is drawn at operation S506. At operation S524, which may be an optional operation based on whether the tip device includes an additional additive assembly as described herein (e.g., additional additive assembly 356), the generated vapor is directed ("drawn") through one or more additional additive structures (e.g., additional additive structures 357*a* and/or 357*b*) of the additional additive assembly, such that the generated vapor is mixed with one or more additional additives in the first air flow. At operation S526, the generated vapor is directed through the outlet end of the first conduit and thus out of the first conduit.

Operations S532-S536 are performed with regard to a second conduit of the tip device, as described herein. At operation S532, the aforementioned second air flow (e.g., air flow 197) is received into the second conduit via an inlet end of the second conduit. As described herein, the effective cross-sectional flow area of the inlet end of the second conduit may be adjustably controlled, via adjustable control of an adjustable flow control assembly, such that the flow rate of the second air flow through the second conduit may be adjustably controlled. In some example embodiments, the inlet end of the second conduit may be closed entirely, such that the flow of the second air flow (e.g., air flow 197) through the second conduit is entirely or substantially entirely (e.g., entirely within manufacturing tolerances and/or material tolerances) nullified, thereby precluding the performance of operations S532-S536.

At operation S534, provided that a second air flow is received into the second conduit in operation S532, the second air flow is directed to flow through the second conduit towards the outlet end of the second conduit, such that the second air flow passes in fluid communication with an additive material that is on a surface that at least partially defines the second conduit. As a result, the additive material releases an additive into the second air flow to form a "mixed air flow" (e.g., "mixed air flow 197*a*") as described herein. At operation S536, the mixed air flow is directed through the outlet end of the second conduit and thus out of the second conduit.

At operation S540, the first and mixed air flows, respectively including a generated vapor and a released additive (where the first air flow may further include an additional additive), are directed to flow through a common conduit (e.g., mixing conduit 370) such that the first and mixed air flows are caused to mix. As a result of such mixing, the generated vapor of the first air flow and the additive of the mixed air flow (and optionally additionally the additional additive of the first air flow) may mix to form a mixed vapor.

At operation S542, the mixed vapor is directed out of the tip device via an outlet of the tip device. Where the tip device is coupled to the aforementioned external source to form an e-vaping device, operation S542 may include directing the mixed vapor out of the e-vaping device.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A tip device for an electronic vaping device (EVD), the tip device comprising:
    a first conduit structure having a surface at least partially defining a first conduit having an inlet end and an outlet end opposite the inlet end, the first conduit structure configured to receive a generated vapor from an external source via the inlet end of the first conduit and direct the received generated vapor through the first conduit towards the outlet end of the first conduit;
    a second conduit structure having a surface at least partially defining a second conduit having an inlet end and an outlet end opposite the inlet end, the second conduit structure configured to receive an air flow from an ambient environment via the inlet end of the second conduit and direct the air flow through the second conduit towards the outlet end of the second conduit, the second conduit structure including an additive material on a surface of the second conduit structure, the additive material including an additive, the additive material configured to release the additive into the air flow directed through the second conduit; and
    an additional additive assembly removably coupled to an inlet end of the first conduit structure and in fluid communication with the first conduit, an inner surface of the additional additive assembly at least partially defining a channel fluidly coupled to the first conduit structure, wherein the additional additive assembly includes at least one additional additive structure extending transversely across the channel between the inner surface of the additional additive assembly and an inner surface of the first conduit structure, the at least one additional additive structure adjacent an outlet end of the additional additive assembly, the at least one additional additive structure configured to release an additional additive into the generated vapor that is directed through the first conduit, such that the air flow directed through the outlet end of the second conduit includes the additive, and the generated vapor directed through the outlet end of the first conduit includes the additional additive, wherein at least an interposing structure of the first conduit structure and the second conduit structure physically isolates the additive material from the first conduit, such that the additive material is configured to release the additive into the air flow directed through the second conduit independently of the generated vapor directed through the first conduit.

2. The tip device of claim 1, further comprising:

an outlet assembly configured to receive the air flow and the generated vapor from respective outlet ends of the first and second conduits, mix the air flow and the generated vapor to establish a mixed vapor, and direct the mixed vapor out of the tip device.

3. The tip device of claim 1, wherein the interposing structure is common to both the first conduit structure and the second conduit structure, such that the interposing structure at least partially defines both the first conduit and the second conduit.

4. The tip device of claim 3, wherein the interposing structure includes opposite surfaces at least partially defining separate conduits of the first conduit and the second conduit.

5. The tip device of claim 1, wherein the interposing structure includes a hollow cylindrical structure having an inner surface and an outer surface extending along a longitudinal axis;

the first conduit is a cylindrical conduit; and the second conduit is an annular conduit surrounding the first conduit and extending coaxially with the first conduit along the longitudinal axis, the second conduit at least partially defined by at least the outer surface of the interposing structure.

6. The tip device of claim 5, wherein the additive material is on the outer surface of the interposing structure.

7. The tip device of claim 1, wherein the additive material includes an adsorbent material.

8. The tip device of claim 1, further comprising:

an adjustable flow control assembly coupled to the inlet end of the second conduit, the adjustable flow control assembly configured to adjustably control an effective cross-sectional flow area of the inlet end to control a flow rate of air drawn into the second conduit via the inlet end of the second conduit.

9. An e-vaping device, comprising:

a vaporizer assembly configured to form a generated vapor; and a tip device in fluid communication with the vaporizer assembly, the tip device including, a first conduit structure having a surface at least partially defining a first conduit having an inlet end and an outlet end opposite the inlet end, the first conduit structure configured to receive the generated vapor from the vaporizer assembly via the inlet end of the first conduit and direct the received generated vapor through the first conduit towards the outlet end of the first conduit;

a second conduit structure having a surface at least partially defining a second conduit having an inlet end and an outlet end opposite the inlet end, the second conduit structure configured to receive an air flow from an ambient environment via the inlet end of the second conduit and direct the air flow through the second conduit towards the outlet end of the second conduit, the second conduit structure including an additive material on a surface of the second conduit structure, the additive material including an additive, the additive material configured to release the additive into the air flow directed through the second conduit; and an additional additive assembly removably coupled to an inlet end of the first conduit structure and in fluid communication with the first conduit, an inner surface of the additional additive assembly at least partially defining a channel fluidly coupled to the first conduit structure, wherein the additional additive assembly includes at least one additional additive structure extending transversely across the channel between the inner surface of the additional additive assembly and an inner surface of the first conduit structure, the at least one additional additive structure adjacent an outlet end of the additional additive assembly, the at least one additional additive structure configured to release an additional additive into the generated vapor that is directed through the first conduit, such that the air flow directed through the outlet end of the second conduit includes the additive, and the generated vapor directed through the outlet end of the first conduit includes the additional additive, wherein at least an interposing structure of the first conduit structure and the second conduit structure physically isolates the additive material from the first conduit, such that the additive material is configured to release the additive into the air flow directed through the second conduit independently of the generated vapor directed through the first conduit; and a power supply section configured to supply power to the vaporizer assembly.

10. The e-vaping device of claim 9, the tip device further including an outlet assembly configured to receive the air flow and the generated vapor from respective outlet ends of the first and second conduits, mix the air flow and the generated vapor to establish a mixed vapor, and direct the mixed vapor out of the tip device.

11. The e-vaping device of claim 9, wherein the interposing structure is common to both the first conduit structure and the second conduit structure, such that the interposing structure at least partially defines both the first conduit and the second conduit.

12. The e-vaping device of claim 11, wherein the interposing structure includes opposite surfaces defining separate conduits of the first conduit and the second conduit.

13. The e-vaping device of claim 9, wherein the power supply section includes a rechargeable battery.

14. The e-vaping device of claim 9, wherein the tip device is reversibly coupled to the vaporizer assembly.

15. The e-vaping device of claim 9, the tip device further including an adjustable flow control assembly coupled to the inlet end of the second conduit, the adjustable flow control assembly configured to adjustably control an effective cross-sectional flow area of the inlet end to control a flow rate of air drawn into the second conduit via the inlet end of the second conduit.

16. A method of operation of a tip device, the tip device configured to be reversibly coupled to an external source, the external source configured to generate a generated vapor, the method comprising:

receiving, at an inlet end of a first conduit at least partially defined by a first conduit structure, the generated vapor from the external source;

directing the received generated vapor through the first conduit towards an outlet end of the first conduit opposite the inlet end of the first conduit;

receiving, at an inlet end of a separate second conduit at least partially defined by a second conduit structure, an air flow from an ambient environment;

directing the air flow through the second conduit in fluid communication with an additive material on a surface of the second conduit, such that an additive is released from the additive material into the air flow independently of the generated vapor directed through the first conduit, and further directing the air flow through the second conduit towards an outlet end of the second conduit opposite the inlet end of the second conduit, wherein an interposing structure of the tip device physically isolates the additive material from the first conduit, such that the additive material releases the additive into the air flow directed through the second conduit independently of the generated vapor directed through the first conduit;

directing the generated vapor in fluid communication with an additional additive assembly removably coupled to an inlet end of the first conduit structure, such that
the additional additive assembly releases an additional additive into the generated vapor that is directed through the first conduit,
the air flow directed through the outlet end of the second conduit includes the additive, and
the generated vapor directed through the outlet end of the first conduit includes the additional additive; and directing the generated vapor directed out of the outlet end of the first conduit and the air flow directed out of the outlet end of the second conduit through a common conduit, such that the generated vapor and the air flow mix to form a mixed vapor;

wherein an inner surface of the additional additive assembly at least partially defining a channel fluidly coupled to the first conduit structure, wherein the additional additive assembly includes at least one additional additive structure extending transversely across the channel between the inner surface of the additional additive assembly and an inner surface of the first conduit structure, the at least one additional additive structure adjacent an outlet end of the additional additive assembly.

17. The method of claim 16, wherein
the interposing structure includes opposite surfaces defining separate conduits of the first conduit and the second conduit.

18. The method of claim 16, wherein
the interposing structure includes a hollow cylindrical structure having an inner surface and an outer surface extending along a longitudinal axis;
the first conduit is a cylindrical conduit; and
the second conduit is an annular conduit surrounding the first conduit and extending coaxially with the first conduit along the longitudinal axis, the second conduit at least partially defined by at least the outer surface of the interposing structure.

19. The tip device of claim 1, further comprising an inlet structure configured to be removably coupled to the inlet end of the additional additive assembly.

20. The tip device of claim 1, wherein:
the at least one additional additive structure includes a first additional additive structure adjacent the inlet end of the additional additive assembly and a second additional additive structure adjacent the outlet end of the additional additive assembly, the channel defined between the first additional additive structure, the second additional additive structure, and the inner surface of the additional additive assembly.

* * * * *